United States Patent
Kalishek et al.

(10) Patent No.: US 11,999,013 B2
(45) Date of Patent: Jun. 4, 2024

(54) PULSED LASER PROCESSING OF MEDICAL DEVICES

(71) Applicant: PlasmaTex, LLC, Denton, TX (US)

(72) Inventors: Jason Kalishek, Denton, TX (US); Arun Nair, Denton, TX (US)

(73) Assignee: PLASMATEX, LLC, Denton, TX (US)

( * ) Notice: Subject to any disclaimer, the term of this patent is extended or adjusted under 35 U.S.C. 154(b) by 0 days.

(21) Appl. No.: 18/090,376

(22) Filed: Dec. 28, 2022

(65) Prior Publication Data
US 2023/0201966 A1     Jun. 29, 2023

Related U.S. Application Data

(60) Provisional application No. 63/294,783, filed on Dec. 29, 2021.

(51) Int. Cl.
*B23K 26/352*     (2014.01)
*A61F 2/30*     (2006.01)
(Continued)

(52) U.S. Cl.
CPC ........ *B23K 26/3568* (2018.08); *A61F 2/3094* (2013.01); *B23K 26/0622* (2015.10);
(Continued)

(58) Field of Classification Search
CPC .............. B23K 26/0624; B23K 26/355; B23K 26/0006; B23K 26/352; B23K 26/3584;
(Continued)

(56) References Cited

U.S. PATENT DOCUMENTS

| 5,558,789 A | 9/1996 | Singh |
| 6,159,832 A | 12/2000 | Mayer |

(Continued)

FOREIGN PATENT DOCUMENTS

| CN | 108754372 | 11/2018 |
| IN | 201711020529 | 12/2018 |

(Continued)

OTHER PUBLICATIONS

Balling, Peter, et al., Short-pulse metal structuring: a method for modifying surface adhesion properties, Proc. of SPIE vol. 6880 (2008), 9 pages.
(Continued)

*Primary Examiner* — Chris Q Liu
(74) *Attorney, Agent, or Firm* — Sheppard, Mullin, Richter & Hampton LLP

(57) ABSTRACT

Systems and methods are provided for generating microscale structures and/or nanoscale structures, surface profiles, and surface chemistries on medical devices. Embodiments disclosed herein utilize exposure of pulsed laser radiation on to a surface of a material by a pulsed laser. The pulsed laser according to embodiments disclosed herein is configured to emit at least one laser pulse toward the surface and thereby modify the profile of the surface in order to selectively promote or inhibit bioactivity and medical functionality of the material. By selectively promoting or inhibiting bioactivity of the material, enhanced biointegration at a cellular level may be achieved. For example, modifying the surface profile and/or surface chemistry of a first substrate material can improve adhesive and/or chemical bonding of the first material to a bioactive second coating material.

15 Claims, 18 Drawing Sheets

(51) Int. Cl.
*B23K 26/0622* (2014.01)
*B23K 26/12* (2014.01)

(52) U.S. Cl.
CPC .... *B23K 26/12* (2013.01); *A61F 2002/30838* (2013.01); *A61F 2002/3084* (2013.01); *A61F 2002/3093* (2013.01); *A61F 2002/30932* (2013.01); *A61F 2002/3097* (2013.01); *A61F 2002/30971* (2013.01)

(58) Field of Classification Search
CPC .. B23K 26/40; B23K 26/0622; B23K 26/364; B23K 26/53; B23K 26/126; B23K 26/046; B23K 26/0648; B23K 26/082; B23K 26/123; B23K 26/127; B23K 26/32; B23K 26/361; B23K 26/60; B23K 26/032; B23K 26/04; B23K 26/0608; B23K 26/0617; B23K 26/0626; B23K 26/0665; B23K 26/073; B23K 26/0821; B23K 26/122; B23K 26/1224; B23K 26/14; B23K 26/244; B23K 26/354; B23K 26/362; B23K 26/38; A61F 2002/0081; A61F 2/38; A61F 2/3094; A61F 2/30767; A61F 2/0077; A61F 2002/3097
USPC ............ 219/121.69, 121.72, 121.61, 121.64, 219/121.67, 121.71, 121.83, 121.85, 219/121.41, 121.63, 121.66, 121.7, 219/121.73, 121.75, 121.8
See application file for complete search history.

(56) References Cited

U.S. PATENT DOCUMENTS

| | | |
|---|---|---|
| 6,312,768 B1 | 11/2001 | Rode et al. |
| 7,103,076 B2 | 9/2006 | Kitaoka et al. |
| 8,486,073 B2 | 7/2013 | Lappalainen et al. |
| 8,728,585 B2 | 5/2014 | Sawada et al. |
| 10,106,880 B2 | 10/2018 | Seghi et al. |
| 10,189,117 B2 | 1/2019 | Seghi et al. |
| 2002/0173778 A1 | 11/2002 | Knopp et al. |
| 2005/0127049 A1 | 6/2005 | Woeste et al. |
| 2005/0173387 A1 | 8/2005 | Fukuyo et al. |
| 2005/0274702 A1 | 12/2005 | Deshi |
| 2006/0039419 A1 | 2/2006 | Deshi |
| 2006/0051522 A1 | 3/2006 | Talton |
| 2006/0138102 A1 | 6/2006 | Sawada et al. |
| 2007/0051706 A1 | 3/2007 | Bovatsek et al. |
| 2007/0225785 A1 | 9/2007 | Park et al. |
| 2008/0124486 A1 | 5/2008 | Sawada et al. |
| 2009/0236323 A1 | 9/2009 | Sun et al. |
| 2010/0047587 A1 | 2/2010 | Itoh et al. |
| 2010/0084384 A1 | 4/2010 | Bovatsek et al. |
| 2010/0143744 A1 | 6/2010 | Gupta et al. |
| 2010/0219506 A1 | 9/2010 | Gupta et al. |
| 2011/0207328 A1 | 8/2011 | Speakman |
| 2011/0248372 A1 | 10/2011 | Kurita |
| 2012/0067855 A1 | 3/2012 | Guo et al. |
| 2012/0328905 A1 | 12/2012 | Guo et al. |
| 2013/0020297 A1 | 1/2013 | Gupta et al. |
| 2013/0197628 A1 | 8/2013 | Barcikowski et al. |
| 2013/0344302 A1 | 12/2013 | Helie et al. |
| 2014/0154526 A1 | 6/2014 | Guo et al. |
| 2014/0239552 A1 | 8/2014 | Srinivas et al. |
| 2014/0273535 A1 | 9/2014 | Gupta et al. |
| 2014/0332499 A1 | 11/2014 | Palmaz et al. |
| 2015/0038313 A1 | 2/2015 | Hosseini |
| 2015/0064407 A1 | 3/2015 | Bruck et al. |
| 2015/0173635 A1 | 6/2015 | Fisk |
| 2015/0367558 A1 | 12/2015 | Brandl et al. |
| 2016/0001396 A1 | 1/2016 | Brandl et al. |
| 2016/0201184 A1 | 7/2016 | Seghi et al. |
| 2017/0182558 A1 | 6/2017 | Shimizu et al. |
| 2017/0260100 A1 | 9/2017 | Kakehata et al. |
| 2019/0283176 A1 | 9/2019 | He et al. |
| 2019/0330064 A1 | 10/2019 | Tour et al. |
| 2020/0009687 A1 | 1/2020 | Guan et al. |
| 2020/0130103 A1 | 4/2020 | Choi et al. |

FOREIGN PATENT DOCUMENTS

| | | |
|---|---|---|
| JP | 2016/202728 | 12/2016 |
| WO | WO 2008/097374 | 8/2008 |
| WO | WO 2012/163351 | 12/2012 |
| WO | WO 2014/025332 | 2/2014 |
| WO | WO 2016097453 | 6/2016 |

OTHER PUBLICATIONS

Brown et al., "Fundamentals of Laser-Material Interaction and Application to Multiscale Surface Modification," Laser Precision Microfabrication, Springer Series in Materials Science 135, 2010, pp. 91-120.

Chen et al., "Surface Modification with Femtosecond Laser." Novel Structured Metallic and Inorganic Materials (2019): 469-483.

Derrien et al., "Rippled area formed by surface plasmon polaritons upon femtosecond laser double-pulse irradiation of silicon: the role of carrier generation and relaxation processes," Appl. Phys. A, Oct. 23, 2013, Accepted Dec. 10, 2013, 5 pages.

Hiraoka et al., "Laser-Induced Sub-Half-Micrometer Periodic Structure on Polymer Surfaces," Applied physics letters, v. 64, (5), 1994, Jan. 31, 3 pages.

Palmieri et al., "Supersonic Retropulsion Surface Preparation of Carbon Fiber Reinforced Epoxy Composites for Adhesive Bonding," Report NF1676L-15433, May 6, 2013, 14 pages, ntrs.nasa.gov/search.jsp?R=20130013699.

Shaikh et al., "Femtosecond laser induced surface modification for prevention of bacterial adhesion on 45S5 bioactive glass." Journal of Non-Crystalline Solids 482 (2018): 63-72.

Yasumaru et al, "Femtosecond-laser-induced nanostructure formed on hard thin films of TiN and DLC," Appl. Phys. A 76, 983-985 (2003); 3 pages.

Zeng et al., "Ultraviolet femtosecond and nanosecond laser ablation of silicon: ablation efficiency and laser-induced plasma expansion." High-Power Laser Ablation V. vol. 5448. SPIE, 2004.

International Search Report and Written Opinion dated Apr. 5, 2023 for International Application No. PCT/US2022/054205, filed Dec. 28, 2022.

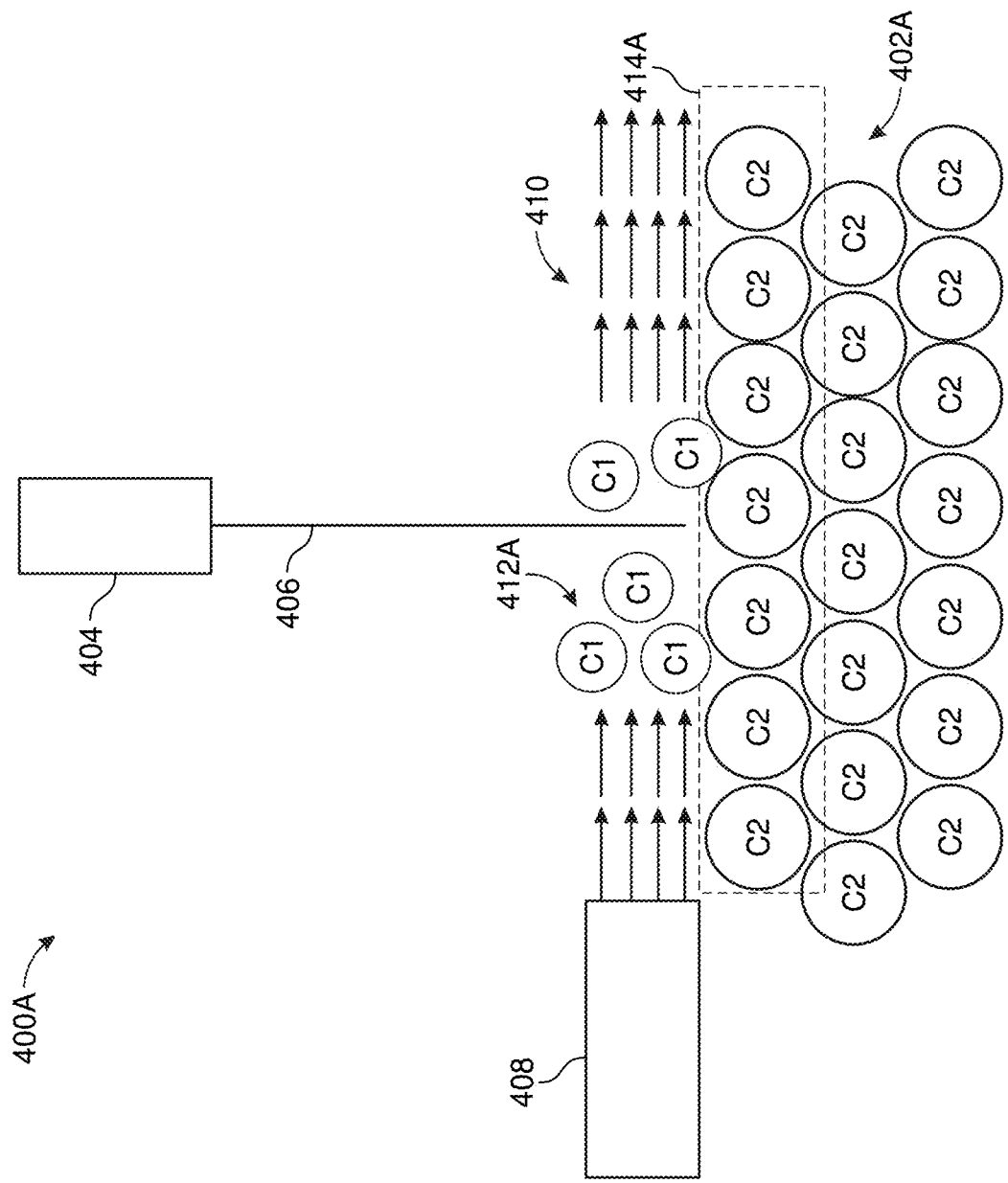

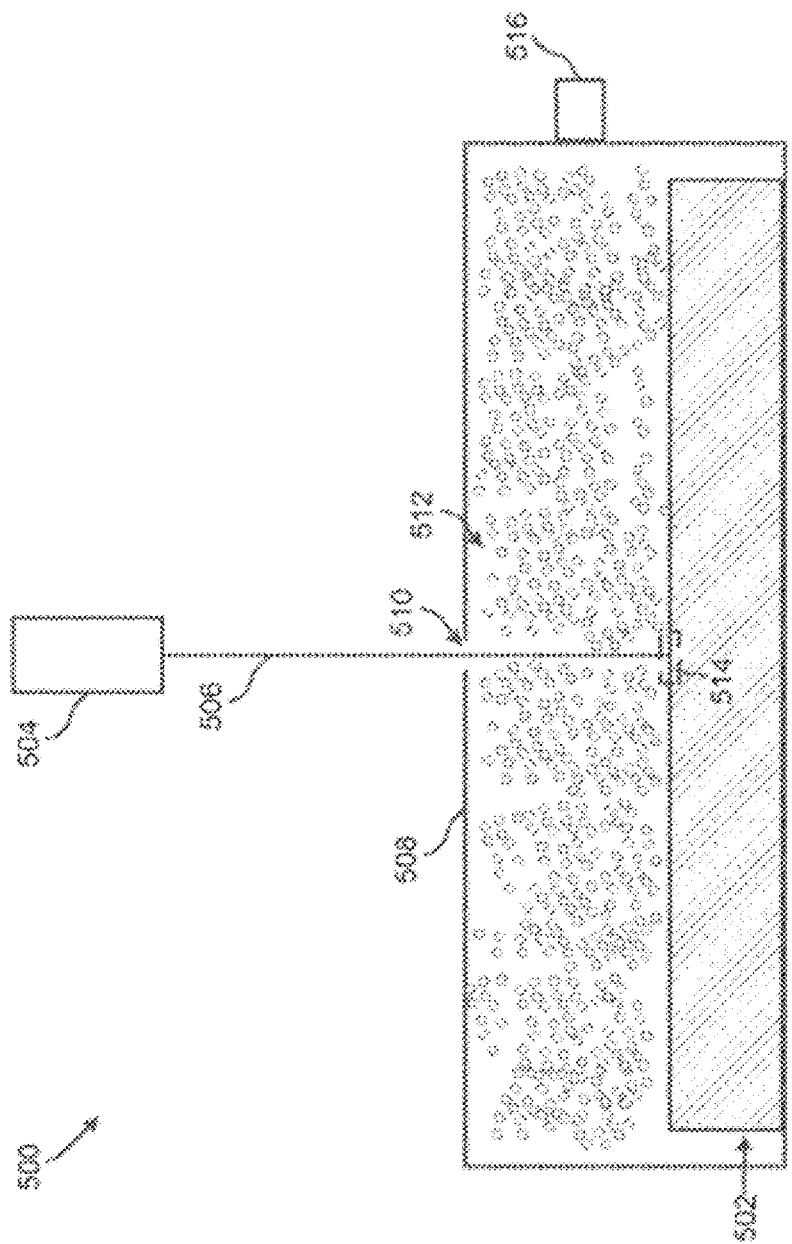

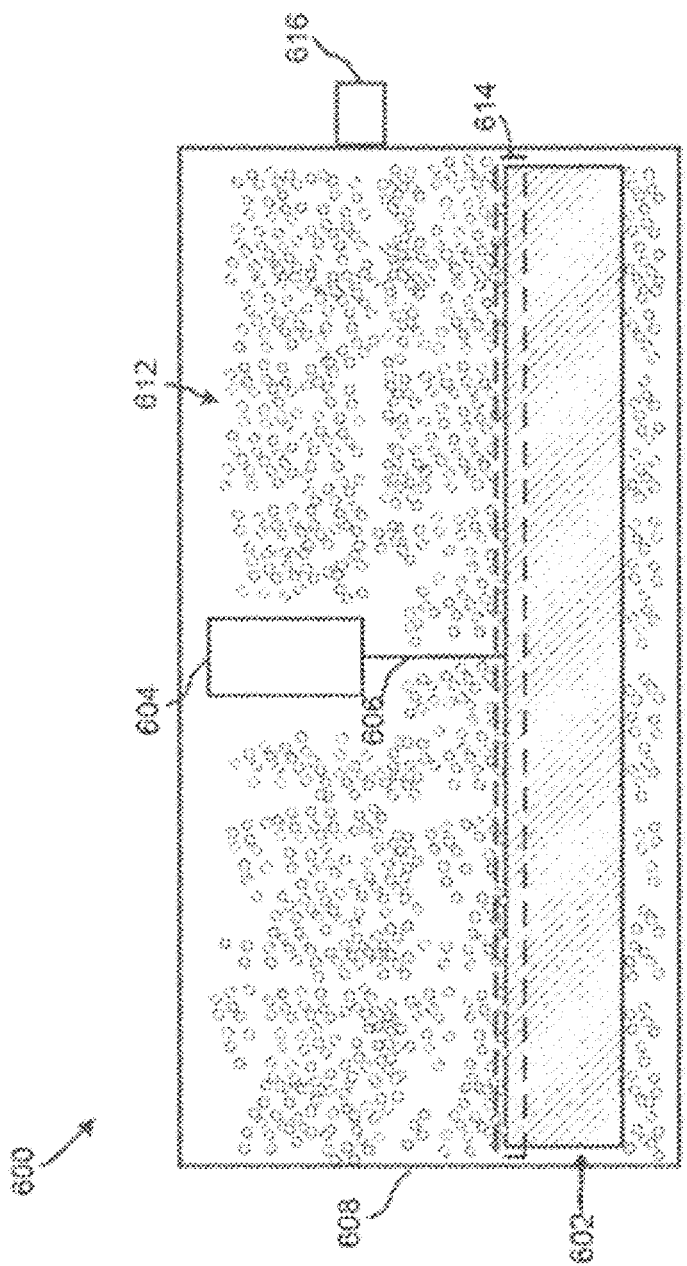

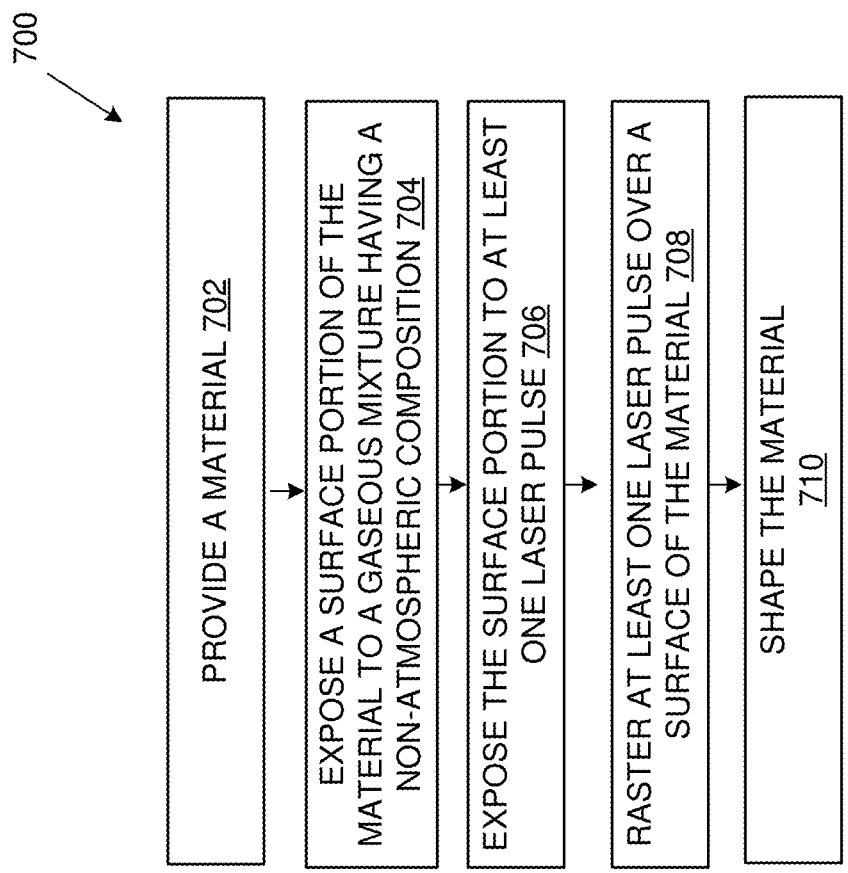

PULSED LASER PROCESSING OF MEDICAL DEVICES

CROSS-REFERENCE TO RELATED APPLICATION

This application claims the benefit of U.S. Provisional Application No. 63/294,783 filed Dec. 29, 2021 and which is hereby incorporated herein by reference in its entirety.

TECHNICAL FIELD

Embodiments disclosed herein generally relate to modifying the surface of medical implants using a pulsed laser to alter their bioactivity. Additionally, various embodiments of the present disclosure relate to modifying the surface chemistry of a material using a pulsed laser. In embodiments, the pulsed laser may be an ultrashort pulsed laser.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

Some of the figures included herein illustrate various embodiments of the disclosed technology from different viewing angles. Although the accompanying descriptive text may refer to such views as "top," "bottom" or "side" views, such references are merely descriptive and do not imply or require that the disclosed technology be implemented or used in a particular spatial orientation unless explicitly stated otherwise.

FIGS. 4A-4B are diagrams illustrating example systems for modifying a specific surface chemistry and surface profile of a material, in accordance with embodiments of the present disclosure.

FIG. 5 is a diagram illustrating another example system for modifying a surface chemistry and surface profile, in accordance with embodiments of the present disclosure.

FIG. 6 is a diagram illustrating another example system for modifying a surface chemistry and surface profile, in accordance with embodiments of the present disclosure.

FIG. 7 is a flow diagram depicting an illustrative method for modifying the surface chemistry and surface profile of a material, in accordance with embodiments of the present disclosure.

Figure 1B:
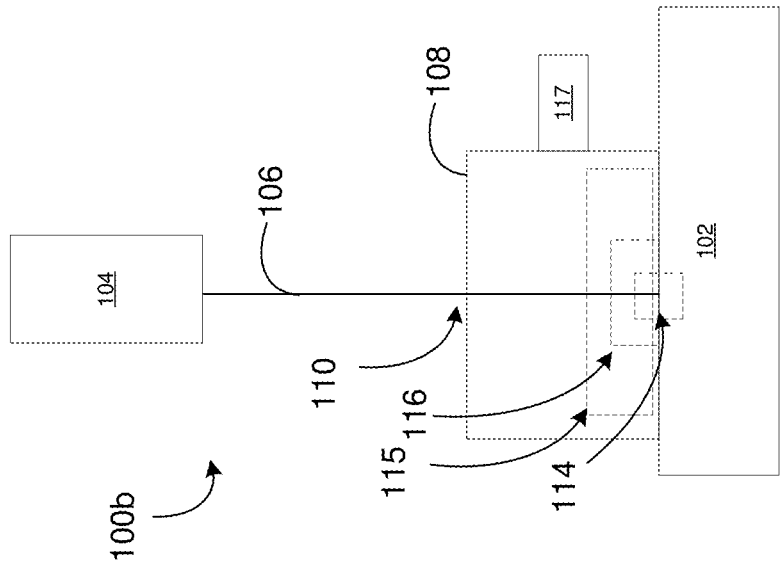
FIGS. 1A-1B are diagrams illustrating an example system for modifying the surface profile and chemistry of a material to selectively promote or inhibit bioactivity in accordance with the embodiments of the present disclosure.

The figures are not exhaustive and do not limit the disclosure or the disclosed embodiments to the precise form disclosed.

DESCRIPTION

Medical implants and non-implantable devices include devices or tissues that are designed for use and/or placement inside and/or on the exterior of the body. Example implants include orthopedic devices (e.g., vertebrae implant, hip implant). Many implants are prosthetics, which are used to replace missing, damaged, malfunctioning or worn body parts. Other implants may be provided to deliver medication to the user, monitor vital signs or body functions, provide support to organs and tissues, or provide other functions. Some implants are intended for permanent placement, while others are intended to be removed from the body after they are no longer needed. Some implants are fabricated using body tissues, while artificial implants, on the other hand, may be made from metals, plastics, ceramics, other materials, or combinations of any or all of the foregoing.

Artificial implants are used extensively to replace damaged or diseased tissues, thereby restoring normal or close-to-normal function to their recipients. While these implants replicate the natural biomechanics of the replaced native tissue at a macro level, there is limited focus on the interaction with the cells and organisms surrounding the implant at the micro level. The current state of science yields implants that at best do little to enhance biointegration at the cellular level and at worst deleteriously affect integration or hinder aseptic techniques.

Bacterial infections pose a significant problem in the field of medical implants. Once an infection sets in, the results are generally catastrophic with high associated morbidity, often requiring serial revisions with multiple washouts and rounds of antibiotics or removal of the device. The infection is generally caused by colonization of the device prior to and/or during implantation, but may occur at any point in the implant's lifecycle. Infection during post-surgery and recovery phases can arise, as can infections years after the device is implanted.

Embodiments disclosed herein may be implemented to use a pulsed laser to treat a surface of a device, such as medical implants, in such a way that would prevent this colonization, retard growth of the colonization, kill infectious microbes, etc. This may significantly decrease infection rates and save patients from the severe costs and morbidity associated with these infections.

Another significant challenge with conventional implants is device failure. This can either arise from inappropriate migration or intrinsic structural failure. Migration can occur when a device loosens from the tissue into which it was surgically implanted. This is most often secondary to a loss of adherence between the device and the tissue substrate. Embodiments disclosed herein may be implemented to texturize outer surfaces of a device, such as, for example, surfaces of medical implants, that are to contact and adhere to tissue into which the device is implanted. This texturing can be implemented to induce a host response to maximize bio-integration and reduce this form of failure.

Structural failure most often occurs secondary to fatigue and stress imparted into the device during manufacture and processing, and/or through corrosion or tarnishing of the base metal/alloy. Embodiments disclosed herein may be implemented to alter the surface chemistry of surfaces of a device with a pulsed laser using a process that produces a corrosion-resistant layer without inducing significant fatigue and stress.

Device failure can also occur following exterior coating delamination, in which an outer surface coating of a device in contact with tissue experiences a loss of adhesion to the device substrate. This type of failure can cause a variety of harmful effects to the recipient of the device, including, but not limited to, inappropriate migration, intrinsic structural failure, device corrosion, release of harmful particulate into the recipient to name a few.

Embodiments disclosed herein may be implemented to solve a long-standing problem of directing cells/organisms to either attach to or not adhere to specific desired area(s) of a medical device. This can be accomplished in various embodiments by treating one or more surfaces of the implant with a pulsed laser to alter the physical or chemical characteristics of such surfaces. Various embodiment disclosed herein may be implemented to improve adhesion (e.g., improve bond strength) of bioactive coatings to device substrates through texturing and/or chemistry modification of a surface of the device substrate to provide increased adhesion (e.g., increased bonding strength). This can be beneficial to various materials, such as for example, osseous minerals (such as hydroxyapatite), metal alloys (such as Ti-6Al-4V), and the like which are commonly deposited onto medical device substrates via coating methods such as thermal spray. The reliable medical performance of the bioactive coating relies on the quality of the surface of the device substrate and/or method of surface preparation prior to applying the bioactive coating to the surface.

Current state of surface treatments utilizes mechanical abrasion, etchants, and other mechanical methods to produce surface textures related to the properties of the materials used to create the surface, such as the grain structure of a metal substrate or the particle size of the abrasive media. Polymers are much softer than the typical mechanical abrasives used, and these methods can therefore result in significant deformation. Also, abrasives embedded as part of the process can alter and/or contaminate the surface chemistry/profile of the material in an undesirable way. Ceramics, on the other hand, may be too hard to respond to abrasive methods or too fragile to survive treatment.

Conventional etchants are also limited in usefulness. The resultant etched surface may be inconsistent (e.g., due to selective removal of areas of the material most susceptible to etching) and the resulting surface texture is limited by the grain size of the material (e.g., in the case of a metal), and crystal size (e.g., in the case of a ceramic).

Embodiments disclosed herein may be implemented to overcome these limitations of the current methods. For example, embodiments may be implemented to produce a three-dimensional surface topography that is not dependent on the base material makeup, chemistry, crystallinity, and/or grain size.

Additionally, most of these conventional mechanical processes are multi-step processes and produce particulate or other contaminants that require subsequent processing to yield a "clean" implant. The steps of these processes are further complicated in applications where medical devices receive coatings, as parts need to be masked, coated, unmasked, and often carefully hand-processed to remove loose or undesirable coating material. Embodiments of the disclosed technology provide a one-step process that should not require further processing.

Embodiments of the present disclosure include systems and methods for modifying the surface profile of medical devices using a pulsed laser to selectively promote or inhibit bioactivity. The systems and methods of the present disclosure can also be utilized for modifying the surface profiles to improve adhesion of bioactive coatings. Thus, embodiments disclosed herein may eliminate the need for traditional steps such as grit blasting, along with the associated steps such as masking, demasking, cleaning, etc., while enabling improved adhesion and manufacturing consistency at reduced cost.

Embodiments of the present disclosure may be configured to use a pulsed laser to replicate or improve upon the natural in vivo conditions thereby facilitating restoration of normal bioactivity. Embodiments of the present disclosure may be configured to use a pulsed laser to selectively induce or retard adherence of cells. Cells may include but are not limited to chondrocytes, osteocytes, ameloblasts, odontoblasts, neural cells, or endothelium cells. In in vivo applications, inducement and/or retardance of adherence of cells (e.g., by repelling) may improve biointegration. In ex-vivo and in vitro applications, this process may allow for the creation of microbiostatic and/or microbicidal surfaces that may adversely affect bacterial biofilm formation, viral particle attachment, organism attachment (fungi, protozoa, bacteria). Example ex-vivo surfaces may include door knobs, orthodontics and other medical equipment and tools, external fixation devices (e.g., external rings, fixation pins, struts for Ilizarov apparatus), braces, tissue culture scaffolds, etc. In some example embodiments, the present systems and methods allow for the creation of tissue scaffolding, such that the scaffold can selectively hinder and/or induce bioactivity. As such, the structures/patterns that can be created according to aspects of the present disclosure can allow for the creation of microbiostatic and/or microbicidal surfaces. The structures/patterns can prevent contamination on devices including but not limited to in vivo, in vitro, and ex-vivo components by adversely affecting bacterial biofilm formation and bacterial attachment. These structures/patterns can also be active against other infectious agents and organisms.

Structures created according to aspects of the present disclosure can have one or more varying depths or heights. In embodiments, structures can have a diameter, width, or footprint dimension of 0.01-999 nm and height 0.01-999 nm. For example, some embodiments herein provide for structures having diameter, width, or footprint dimension of 0.01-700 nm, 0.1-600 nm, or 0.1-400 nm and height 0.01-999 nm. Structures created herein can have rounded, concave, triangular, pyramidal, or other shaped surface footprint or combinations thereof. The structures created herein may be ablation-generated (e.g., creation of negative space through material removal), as well as additive profile generation (e.g., through structure growth). Structures created herein can have rounded, concave, triangular, pyramidal, trench, or other shaped or pitched slope or combinations thereof. For example, structures can have a pitch of 10-400 nm. A pitched structure may have 0-85 degrees pitch peak. As another example, structures can have a trench extending linearly or comprise one or more curves. For example, trenches may have a width of 0.01-999 nm and a depth of 0.01-999 nm. Trenched structures may also extend continuously or semi-continuously corresponding to exposure to the pulsed laser. Structures created according to aspects of the present disclosure can have a microstructure (also referred to herein as microscale structures) diameter of 0.01-999 micrometers, width of 0.01-999 micrometers, and height of 0.01-999 micrometers. For example, some embodiments herein provide for structures having diameter, width, or footprint dimension of 0.01-10 micrometers, 1-10 micrometers, or 2-7.5 micrometers and height 0.01-999 micrometers. Similarly, the trenches may have a width and depth in the micrometer scale as set forth above. Structures created herein can have one or more overhangs, cutouts, carveouts, chamfer, beveling. In some embodiments, one or more patterns of structures can be created according to aspects of the present disclosure. In some embodiments, the patterns include even or uneven spacing (or combinations thereof). According to aspects of the present disclosure, periodic nanostructures (also referred to herein as nanoscale structures) can be created having one or more periodic patterns. In some embodiments, periodic nanostructure can have a periodic nanostructure spacing of 0.01-999 micrometers. In some embodiments, the periodic nanostructures can have spacing of 10-5000 nm. In some embodiments, the respective nanostructures in the periodic nanostructures can have the same or different heights. For example, the nanostructures can have heights between 1-999 nm.

The process can modify the surface chemistry of the device by applying the pulsed laser to a material surface under a non-atmospheric gas, proximal liquid or plasma layer, or transmissive solid film, thereby generating desired characteristics selected from a group consisting of but not limited to hardness, corrosivity, environmental resistivity, chemical reactivity, and photocatalysis. In some embodiments, a desired characteristics may include improved hardness (e.g., titanium nitride), corrosion prevention (e.g., Titanium ceramide, Titanium carbide), or induce photocatalysis (e.g., titanium dioxide).

According to aspects of the present disclosure, in some embodiments, superhydrophobic or superhydrophilic surfaces can be created. In some embodiments, the porosity of the surfaces can be adjusted. In some embodiments, the adhesive properties of the surfaces can be adjusted. In some embodiments according to aspects of the present disclosure, superoleophobic or superoleophilic surfaces can be created.

Embodiments disclosed herein may include a surface three-dimensional topography which may be random or patterned at a micrometer and/or nanometer scale which does not rely on grain structure, crystal structure or other inherent material features for the three-dimensional topography to be produced. In some embodiments, the randomness of the structure may be characterized, for example, as similar to a Mandelbrot fractal.

Cell/organism activity/direction is enabled or prohibited by creation of three-dimensional topography on the surface of a material. The topography created is specifically created to have an interaction at the cell/organism level. The surface created may have a completely random appearance or may have patterns of surface topography depending on the activity required.

In an embodiment of the present disclosure, a system for modifying the surface profile and chemistry of a material includes a material. The material includes a surface portion having a surface profile and chemistry. Additionally, the system includes a pulsed laser configured to emit at least one laser pulse. At least one laser pulse is directed to interact with at least the surface portion, thereby modifying the surface profile and chemistry of the surface portion in order to selectively promote or inhibit bioactivity at surface portion of the material.

In another embodiment of the present disclosure, a system for modifying the surface profile and chemistry of a material includes a material. The material includes a surface portion having a surface profile and chemistry. The system also includes mixture introducer configured to provide a gaseous, solid, liquid, and/or plasma mixture. The mixture introducer is configured to introduce a gaseous, solid, liquid, and/or plasma mixture having a non-atmospheric composition across the surface portion of the material. In some embodiments, the mixture introducer may be configured to induce a laminar flow of the gaseous, solid, liquid, and/or plasma mixture, having a non-atmospheric composition, across the surface portion of the material. Additionally, the system includes a pulsed laser configured to emit at least one laser pulse. At least one laser pulse is directed to pass through the portion of mixture onto at least the surface portion of the material, thereby modifying the surface profile and chemistry of the surface portion in order to selectively promote or inhibit bioactivity at the surface portion of the material.

In yet another embodiment of the present disclosure, a system for modifying the surface profile and chemistry of a material includes a first material. The first material includes a surface portion having a surface profile and chemistry. The system also includes a second material proximal to the first material. The second material can include at least one of a solid, gaseous, plasma, and/or liquid material. The second material can be selected based on a desired characteristics of the first material. In some embodiments, the second material (e.g., the type of material or mixture thereof) is selected based on a at least one of desired hardness, environmental resistivity, and photocatalysis of the medical device. Examples of second materials includes, but are not limited to, osseous minerals (such as hydroxyapatite), sprayed metal alloys (such as Ti-6Al-4V), and the like. The second material can be deposited on or proximal to the first material as a layer, coating, or bath. The second material can be deposited as a thin layer or coating of a solid substance using physical vapor deposition, sputtering, evaporative techniques, electron beam deposition, chemical solution deposition, chemical vapor deposition, thermal spray, cold spray, dip coating, spin coating and/or the like. Additionally, the system includes a pulsed laser configured to emit at least one laser pulse. At least one laser pulse is emitted to interact with at least the surface portion of the first material, thereby modifying the surface profile and/or chemistry of the surface portion of the first material in order to improve adhesive and/or chemical bonding of the first material to a second material. This results in an improvement of the bioactivity, functionality, and/or reliability of the second material as a coating over the first material. In an illustrative example, osseous minerals and/or sprayed metal alloys may be examples of a second material proximal to the first material that can be applied as coatings over the modified surface of the first material. In this example, the pulsed laser may be applied to modify the surface profile and chemistry of a surface portion of the first material surface, thereby improving the adhesion of the osseous minerals and/or sprayed metal alloys coating materials (e.g., bioactive coating materials) to the modified surface of the first material.

Example materials, gaseous mixtures, liquid mixtures, pulsed lasers, systems and methods for applying the pulsed laser light, are described, for example, in U.S. patent application Ser. No. 14/587,455, filed on Dec. 31, 2014, now U.S. Pat. No. 10,189,117, and U.S. patent application Ser. No. 15/077,352, filed on Mar. 22, 2016, now U.S. Pat. No. 10,106,880, the entire disclosures of which are incorporated by reference herein in their entirety.

Figure 1A:
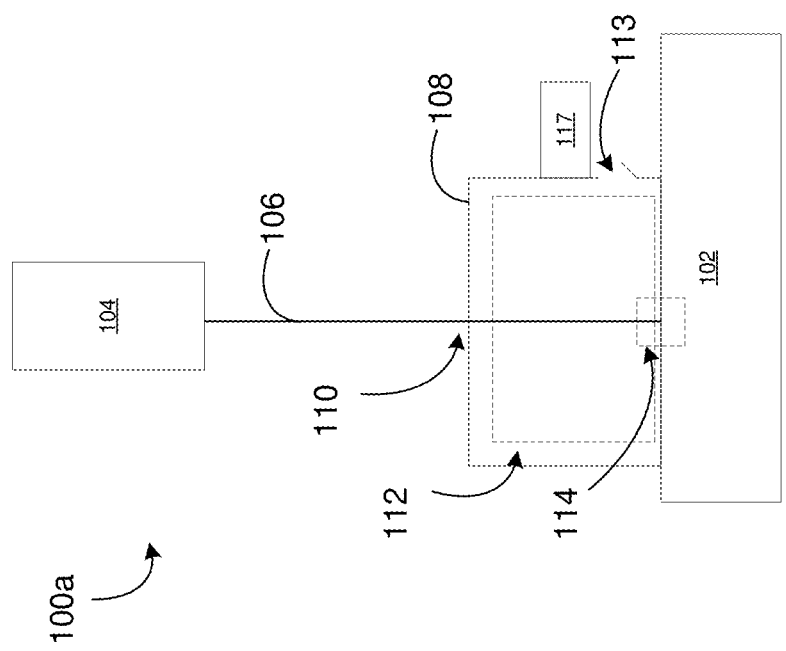

FIGS. 1A-1B are diagrams illustrating an exemplary embodiment of a system 100a (FIG. 1A) and system 100b (FIG. 1B) for modifying the surface profile and chemistry of a material 102 to selectively promote or inhibit bioactivity in accordance with the embodiments of the present disclosure. The material can include one or more metallic substances and a number of non-metallic solid surfaces including, but not limited to, ceramics and polymers. In some embodiments, the material 102 can be aluminum 2024, aluminum 5083, nickel, tungsten, cobalt-chromium, stainless steel, steel HY80, steel HY100, 1018 carbon steel, titanium, titanium 6-4 (also referred to as Ti-6Al-4V), superalloys such as Monel and Inconel, alloys of these metals, etc. As shown in FIGS. 1A-1B, in addition to the material 102, the system 100a, 100b, includes a pulsed laser 104 that emits a laser beam having at least one laser pulse 106 and an enclosure 108 that includes an aperture 110, and at least one of a gaseous mixture 112 having a non-atmospheric composition (shown in FIG. 1A), a liquid substance 115 or mixture (shown in FIG. 1B), and a solid substance 116 (shown in FIG. 1B). The enclosure 108 may be made of different materials, including, but not limited to: various plastics, metals, ceramics, glasses, and/or the like. In some embodiments, processes described herein can be accomplished in ambient atmosphere. In other embodiments, the enclosure 108 can allow for performing the methods described herein in other environments (e.g., in a vacuum, or varied compositions of gases at varied pressures).

In the embodiments shown in FIG. 1A, the laser pulse 106 from the pulsed laser 104 is directed through the aperture 110 and through the gaseous mixture 112 onto the surface portion 114. The pulsed laser 104 can be tuned such that the energy irradiance of the laser pulse 106 is sufficient to convert the surface portion 114 to a plasma state. While the surface portion 114 is in a plasma state, a portion of the gaseous mixture 112 located near the surface portion 114 interacts with the surface portion 114. After the laser pulse 106 no longer irradiates the surface portion 114, the interaction of the surface portion 114 and the portion of the gaseous mixture 112 results in an altered surface chemistry of the surface portion 114.

In embodiments, the system 100 can include a processor, and a memory coupled to the processor, for example, communicatively coupled to the pulsed laser 104. The processor may be implemented, for example, as part of computing system 1100 described in connection with FIG. 11. The memory can be configured to store instructions, which when executed by the processor, cause the processor to perform operations including activating the pulsed laser 104 and providing a control signal for controlling the operation of the pulsed laser 104. In embodiments, the control signal can be adjusted so that a variety of different surface effects are created, for example, by adjusting laser operating parameters of the pulsed laser 104 to tune the laser pulse 106. Controlled tuning of the laser pulse can be used to provide desired modifications of the surface portion 114. A number of laser parameters that may be varied (e.g., tuned), including, but not limited to: processing patterns, laser pulse duration, laser pulse frequency, laser wavelength, laser beam profile, laser irradiance (laser power), the polarization of the laser beam, the diameter of the laser spot on the material to be altered, a distance between the laser and the material, the depth of laser penetration into the surface being processed, and laser angle to material surface in order to alter the resultant surface structure to achieve the desired level or transformation of surface adhesion and/or chemical interfacial properties.

Additionally or alternatively, the enclosure 108 may include a liquid substance 115 (shown in FIG. 1B) that is located proximal to the surface portion 114. In embodiments, the enclosure 108 may be used to contain the liquid substance. However, in other embodiments, an enclosure 108 may not be used in the system 100a, 100b. In embodiments, the liquid may be a mist, an aerosol, a condensate, a pooling of liquid on the surface portion 114 and/or the like that is enclosed by the enclosure 108 or proximal to the surface portion 114 when an enclosure 108 is not used.

When the liquid substance 115 is proximal to the surface portion 114, the pulsed laser 104 is directed through the liquid substance 115 onto the surface portion 114. The energy irradiance of the laser pulse 106 is sufficient to convert the surface portion 114 to a plasma state. While the surface portion 114 is in a plasma state, a portion of the liquid substance 115 located proximal the surface portion 114 interacts with the surface portion 114. After the laser pulse 106 no longer irradiates the surface portion 114, the interaction of the surface portion 114 and the portion of the liquid substance 115 results in an altered surface chemistry of the surface portion 114. For example, the liquid may be carbon (e.g., liquid hydrocarbon) and the surface chemistry may be, for example, titanium, tantalum, hafnium, zirconium, silicon, aluminum, etc. As such, after the laser pulse 106 no longer irradiates the surface portion 114, the altered surface chemistry of the surface portion 114 may be one or more metal carbides, for example, titanium carbide, tantalum carbide, hafnium carbide, zirconium carbide, silicon carbide and/or the like.

Additionally or alternatively, a solid substance 116 (shown in FIG. 1B) may be disposed proximal to the surface portion 114. In these embodiments, the system 100a, 100b, may or may not include the enclosure 108. The solid substance 116 may be a thin layer or coating that is applied to the surface portion 114. In embodiments, a thin layer or coating of a solid substance 116 may be applied to the surface portion 114 using physical vapor deposition, sputtering, evaporative techniques, electron beam deposition, chemical solution deposition, chemical vapor deposition, spin coating and/or the like.

When the solid substance 116 is proximal to the surface portion 114, the pulsed laser 104 is directed through the solid substance 116 onto the surface portion 114. The energy irradiance of the laser pulse 106 is sufficient to convert the surface portion 114 to a plasma state. While the surface portion 114 is in a plasma state, a portion of the solid substance 116 located proximal the surface portion 114 interacts with the surface portion 114. After the laser pulse 106 no longer irradiates the surface portion 114, the interaction of the surface portion 114 and the portion of the solid substance 116 results in an altered surface chemistry of the surface portion 114. For example, the solid may be carbon, boron, etc. and the surface chemistry may be, for example, titanium, hafnium, zirconium, silicon, aluminum, etc. In embodiments where boron is used, after the laser pulse 106 no longer irradiates the surface portion 114, the altered surface chemistry of the surface portion 114 may be one or more metal borides, for example, titanium diboride, hafnium diboride, aluminum diboride and/or the like.

As stated above, the energy irradiance of the laser pulse 106 is sufficient to convert the surface portion 114 to a plasma state. The energy irradiance of the laser pulse 106 required to convert the surface portion 114 to a plasma state may depend on the surface chemistry of the surface portion 114. In embodiments, the surface chemistry of the surface portion 114 may be titanium, $Fe_2O_3$, a nickel alloy, copper, ceramic coated steel, aluminum, tantalum, hafnium, zirconium, silicon and/or the like. In order to turn one of these example surface chemistries into a plasma state, the peak pulse power of the pulsed laser 104 may exceed 10 microjoules. This parameter, however, may be varied and is not meant to be limiting.

In addition to the power of the pulsed laser 104, other parameters of the pulsed laser 104 may be varied, as long as the parameters of the pulsed laser 104 are capable of turning the surface portion 114 into a plasma state. Examples of other laser parameters that may be varied include, but are not limited to, pulse duration, wavelength, angle of incidence, spot size (i.e., the diameter of the cross section of the laser beam 106), and frequency of the laser pulses 106 if the pulsed laser 104 emits more than one laser pulse 106. Examples of each of the parameters that are capable of turning the surface portion 114 into a plasma state when the peak pulse power exceeds 10 microjoules include a duration less than or equal to 1,000 femtoseconds, a wavelength between 100 nanometers (nm) and 3000 nm, angles of incidence greater than 0 degrees and less than 90 degrees, spot sizes between 5 microns and 100 microns and between 5 microns and 5000 microns and frequencies between 50 kilohertz and 200 kilohertz. As another example, the pulsed laser can be a ultrashort pulsed laser. The pulsed laser can emit ultra-short pulses of energy on the order of femtoseconds (fs) to restructure or texturize a surface portion 114 a thermally with a desired texture or three dimensional structure which avoids, minimizes, or reduces damaging the restructured or texturized material. The pulsed laser can include the following parameters: a duration between 850 fs and 550 fs, a wavelength between 1850 nm and 1240 nm, an angle of incidence between 0 and 20 degrees, a spot size between 85 microns and 55 microns, a frequency between 120 kilohertz and 80 kilohertz, a pulse energy between 40 µJ and 25 µJ, and an average power between 4 Watts and 2 Watts. As even another example, the pulsed laser can be a ultrashort pulsed laser and include the following parameters: a duration between 770 fs and 630 fs, a wavelength between 1705 nm and 1395 nm, an angle of incidence between 0 and 10 degrees, a spot size between 77 microns and 63 microns, a frequency between 110 kilohertz and 90 kilohertz, a pulse energy between 36 µJ and 28 µJ, and an average power between 3.6 Watts and 2.8 Watts. As another example, one embodiment can use the following parameters: Raydiance fiber laser, spot size of 70 µm, pulse duration of 700 fs, pulse energy of 32 µJ, average power of 3.2 W, pulse frequency of 100 kHz, wavelength of 1550 nm. However, these are only examples and not meant to be limiting.

In embodiments, the pulsed laser 104 may be rastered over the surface of the material 102. As such, the system 100a, 100b can include a rastering system (e.g., a computing system, such as computing system 1100 of FIG. 11, configured to execute a rastering pattern of pulsed laser 104) adapted for controlling the rastering of laser energy output of the pulsed laser 104 over the surface portion 114 (or other target area thereof). It can be understood that the laser beam can be rastered, in a predetermined path (e.g., serpentine), to a predetermined depth, over multiple passes, and on a predetermined angle to the target surface. In some nonlimiting examples, the raster pattern can be of a circle, or a square. In some examples, the pulsed laser 104 can be applied at a single, double, triple, etc. pass. In systems 100a and/or 100b, memory can include instructions, which when executed by the processor, cause the processor to generate a rastering signal for rastering the laser energy output of the pulsed laser 104. In some embodiments, the pulsed laser 104 may be coupled to one or more actuators of the rastering system for rastering of the laser over the material 102. In some embodiments, the material 102 can be translated and/or rotated along one or more axes by one or more translation and/or rotation module (e.g., by rotating tray, x-y axis table, etc.) such that the pulsed laser 104 can be rastered over the material 102. In some embodiments, an angle of incidence of the laser pulse 106 can be varied. Accordingly, more than the surface chemistry of the surface portion 114 may be modified using such techniques. The pulsed laser 104 may be rastered over the surface of the material 102 at different speeds and in different patterns. For example, the pulsed laser 104 may be rastered over the surface of the material 102 at speeds of 10 millimeters per second (mm/s), 20 mm/s, 30 mm/s and 40 mm/s, etc. and/or in square patterns, linear patterns, cross-hatch patterns, patterns that pass over a portion of the surface multiple times, etc. Again, however, these are only examples and not meant to be limiting. Instead, the pulsed laser 104 may be rastered at any speed and pattern, as long as the pulsed laser 104 is capable of turning the surface portion 114 into a plasma state.

The diameter of the aperture 110 can be different sizes, as well. In embodiments, the diameter of the aperture 110 is dependent on the spot size of the laser pulse 106 and has a diameter larger than the spot size. Additionally, in embodiments, the aperture 110 has a diameter large enough so that the laser pulse 106 does not experience diffraction as the laser pulse 106 passes through the aperture 110. As such, the energy irradiance of the laser pulse 106 can be focused on the surface portion 114.

Alternatively, in embodiments, the aperture 110 is replaced by a window or other material that is generally optically transparent to the wavelength of the laser pulse 106. As such, the energy irradiance of the laser pulse 106 can pass through the window or other material that is generally optically transparent at the wavelength of the laser pulse 106 and be focused on the surface portion 114.

As shown, the enclosure 108 encloses the gaseous mixture 112 that has a non-atmospheric composition. As used herein, the term "non-atmospheric composition" means a gaseous mixture having a compositional make-up that differs from the ambient atmospheric composition surrounding the systems disclosed herein. For example, in general the atmospheric composition of the Earth's atmosphere is about 78% nitrogen and about 21% oxygen (nitrogen and oxygen are about 99% of the atmospheric composition). As such, exemplary non-atmospheric compositions include (1) a gaseous mixture having greater than 78% nitrogen or less than 78% nitrogen, (2) a gaseous mixture having greater than 21% oxygen or less than 21% oxygen, and (3) a gaseous mixture having more than 95% of nitrogen and oxygen combined or less than 95% of nitrogen and oxygen combined, including gaseous mixture including 0% nitrogen and/or oxygen. Gases included in the gaseous mixtures 112 may also include, but are not limited to, argon and/or hydrogen. However, these are only examples and not meant to be limiting. In embodiments, the gaseous mixture 112 is chosen so that after the interaction of the gaseous mixture 112 with the surface chemistry in a plasma state, a desired altered surface chemistry is obtained. Examples of these desired interactions are discussed below in FIGS. 2A-2B and 4A-4B.

To enclose the gaseous mixture 112, the enclosure 108 can be secured over the surface portion 114 and filled with the gaseous mixture 112. In embodiments, the enclosure 108 is filled with the gaseous mixture 112 by injecting the gaseous mixture 112 into the enclosure 108 through the aperture 110. The aperture 110 may include a closing mechanism so the gaseous mixture 112 cannot escape through the aperture 110 when the pulsed laser 104 is not in use. In other embodiments, the gaseous mixture 112 is introduced into the enclosure 108 through another opening 113 in the enclosure 108. The opening 113 is optional and need not be included in some embodiments, for example, where the gaseous mixture 112 is injected through aperture 110 as described above. Similarly, in embodiments, the opening 113 may include an optional closing mechanism (shown as a dashed line to indicate that the closing mechanism is optional) so the gaseous mixture 112 cannot escape through the opening 113 of the enclosure 108. Whether the gaseous mixture 112 is injected via aperture 110 or opening 113, the enclosure 108 assists in retaining the gaseous mixture in contact with the surface portion. This is useful in many scenarios including when the non-atmospheric gaseous mixture is lighter than the surrounding atmospheric gaseous mixture and when the non-atmospheric gaseous mixture is at a higher pressure than the surrounding atmospheric gaseous mixture.

In embodiments, when an enclosure 108 is used, a liquid substance may be introduced into the enclosure 108 using methods similar to the methods for introducing a gaseous mixture 112 into the enclosure 108. In further embodiments, other materials such as plasmas, gels, pastes (or other low-viscosity materials) and other materials may be introduced into the enclosure 108 using similar methods as described above for introducing a gaseous mixture 112 into the enclosure 108. In still further embodiments, solids may also be applied such as, for example, in the form of films or tapes that can be adhered to the surface prior to treatment. Other solid forms can also be adhered or fastened to the surface prior to treatment.

In addition, the system 100a, 100b, may include a filter 117 coupled to the enclosure 108. In embodiments, the filter 117 is capable of filtering an undesirable substance from the gaseous mixture 112 and/or liquid substance. For example, if a compound is expelled from the surface portion after the laser pulse 106 irradiates the surface portion, the filter 117 can be designed to filter the compound from the gaseous mixture 112, so that the interaction between the gaseous mixture 112 and the surface portion 114 may be more controlled.

In addition, the system 100a, 100b, may include an environmental module to monitor and/or control one or more environmental conditions around the surface portion 114, the pulsed laser 104, the material 102, and/or the enclosure 108. The environmental module may be provided as part of or communicatively coupled to a computing system (e.g., computing system 1100 of FIG. 11). It should be understood that environmental conditions can be varied, for example at the sample surface during operation of the pulsed laser 104. For example, environmental conditions that can be varied may include temperature, barometric pressure, the composition of a gaseous or other mixture adjacent to the surface portion 114. This change in environmental conditions can be used to alter the resultant surface (e.g., surface profile) at the surface portion 114 in accordance with aspects of the present disclosure.

In embodiments, the system 100a, 100b may include a profilometer (e.g., laser profilometer) configured to measure the depth or smoothness of the surface portion 114. In some embodiments, the profilometer may measure a first depth or height of the surface portion 114 and generate a profilometer signal based on the measurement. The profilometer signal may be provided to a computing system for controlling system 100a, 100b according to the profilometer signal. For example, this may allow a second (e.g., specific) depth or height of the surface portion may be created, such as of a structure in the surface portion. As such, a pulsed laser control signal can be based on a profilometer signal.

In some embodiments, the system 100a, 100b may be configured to utilize absorption spectroscopy techniques (e.g., spectral reflectance and the like) to measure the depth or smoothness of the surface portion 114. Surface profiles of the surface portion 114 created by the systems 100a, 100b yield specific absorption, reflectance, and/or transmittance spectra, and as such absorption spectroscopy techniques may be implemented to evaluate the surfaces. The absorption spectroscopy techniques may be implemented separately or along with a profilometer as set forth above. In some embodiments, an electromagnetic radiation source and a detector are provided. A reference spectrum of the source is measured by the detector without the surface portion 114 and then a target spectrum is measured based on irradiating the surface portion 114 with the source. In some embodiments, a reflected spectrum is measured by the detector, while in other embodiments a transmitted spectrum through the surface portion 114 is measured. A comparison of the target spectrum with the reference spectrum may be used to determine an absorption spectrum of the surface portion 114. Similarly, a reference reflectance and/or transmittance may be used to determine a reflectance spectrum and/or transmittance spectrum of the surface portion 114. In the case of reflectance, a detector may be positioned on the same side of the surface portion 114 as the source. In the case of transmission, the surface portion 114 may be between detector and source along the optical axis.

The electromagnetic radiation source may include one or more sources such that the reference spectrum covers the entire electromagnetic spectrum and/or a desired portion thereof. In some embodiments, the optical axis of the source and the detector may be normal with the surface portion 114, while in other embodiments the optical axis of the source and the detector may be at an angle off normal. In some examples, the angle at which the detector is off normal may be varied over a hemispherical region of the surface portion 114 (e.g., for measuring a bidirectional reflectance distribution function and/or bidirectional transmittance distribution function).

Figure 2A:
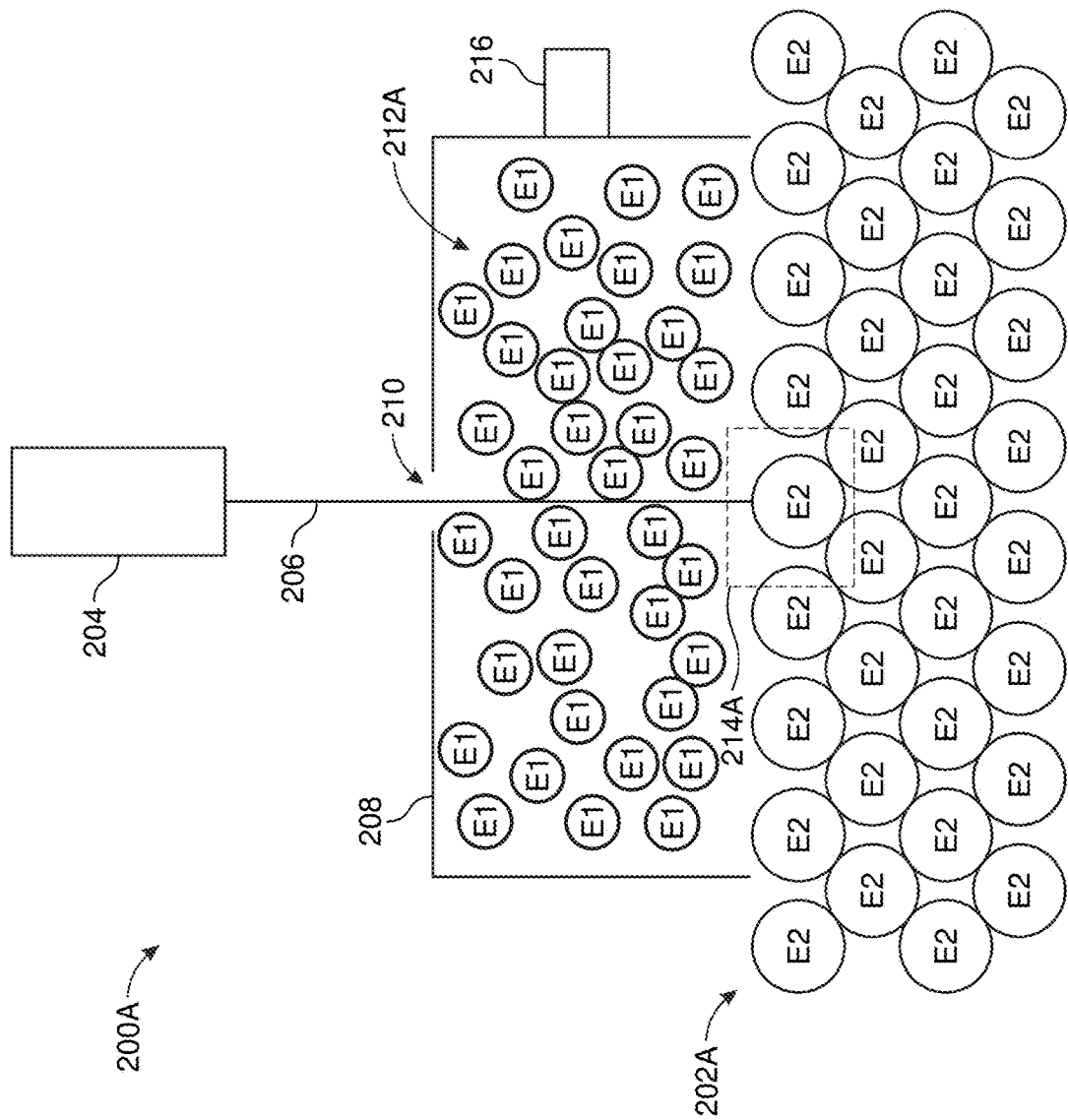
FIGS. 2A-2B are diagrams illustrating example systems for modifying a specific surface chemistry and surface profile of a material, in accordance with embodiments of the present disclosure.

FIG. 2A is a diagram illustrating an example system 200A for modifying a specific surface chemistry of a material 202A, in accordance with embodiments of the present disclosure. The system 200A includes a material 202A, a pulsed laser 204 that emits at least one laser pulse 206 and an enclosure 208. The enclosure 208 includes an aperture 210 and a gaseous mixture 212A having a non-atmospheric composition. The laser pulse 206 from the pulsed laser 204 is directed through the aperture 210 and through the gaseous mixture 212A onto the surface portion 214A. The gaseous mixture 212A and surface portion 214A may be substantially similar to the gaseous mixture 112 and the material 102 (FIG. 1A), respectively.

Alternatively and similar to above, in embodiments, the aperture 210 is replaced by a window or other material that is generally optically transparent to the wavelength of the laser pulse 206. As such, the energy irradiance of the laser pulse 206 can pass through the window or other material that is generally optically transparent at the wavelength of the laser pulse 106 and be focused on the surface portion 114.

In embodiments, the pulsed laser 204 can have some or all of the same characteristics as the pulsed laser 104 shown in FIGS. 1A and 1B. As shown, the gaseous mixture 212A is composed of a first element composition, for example nitrogen, and the surface chemistry of the surface portion 214A is a second element composition, for example titanium. In embodiments, the second element composition may be a titanium oxide, pure titanium that does not include an oxide layer and/or a titanium alloy other than titanium nitride. In some embodiments, the gaseous mixture 212A has a concentration of 100% nitrogen, in other embodiments, the gaseous mixture 212A has a concentration of less than 100% nitrogen, for example, including one or more elements with nitrogen. Furthermore, in some embodiments, the gaseous mixture 212A may comprise an elemental composition as set forth above with respect to gaseous mixture 112 of FIG. 1A. Similarly, while the surface chemistry of the surface portion 214A may be composed of 100% titanium, in other embodiments, the surface chemistry has a concentration of less than 100% titanium. Furthermore, in some embodiments, the surface portion 214A may be composed of materials as set forth above with respect to surface portion 114 of FIG. 1A.

The energy irradiance of the laser pulse 206 is sufficient to convert the second element composition (e.g., titanium in this example) of the surface portion 214A to a plasma state. While the surface portion 214A is in a plasma state, a portion of the first element composition (e.g., nitrogen in this example) in the gaseous mixture 212A located near the surface portion 214A interacts with the titanium of the surface portion 214A. After the laser pulse 206 no longer irradiates the surface portion 214A, the interaction of the titanium and the nitrogen results in an altered surface chemistry of the surface portion 214A.

Additionally, the system 200 may include a filter 216 coupled to the enclosure 208. In embodiments, the filter 216 is capable of filtering an undesirable substance from the gaseous mixture 212 similar to the filter 117 (FIG. 1B). Accordingly, the interaction between the gaseous mixture 212 and the surface portion 214 may be more controlled.

Figure 2B:
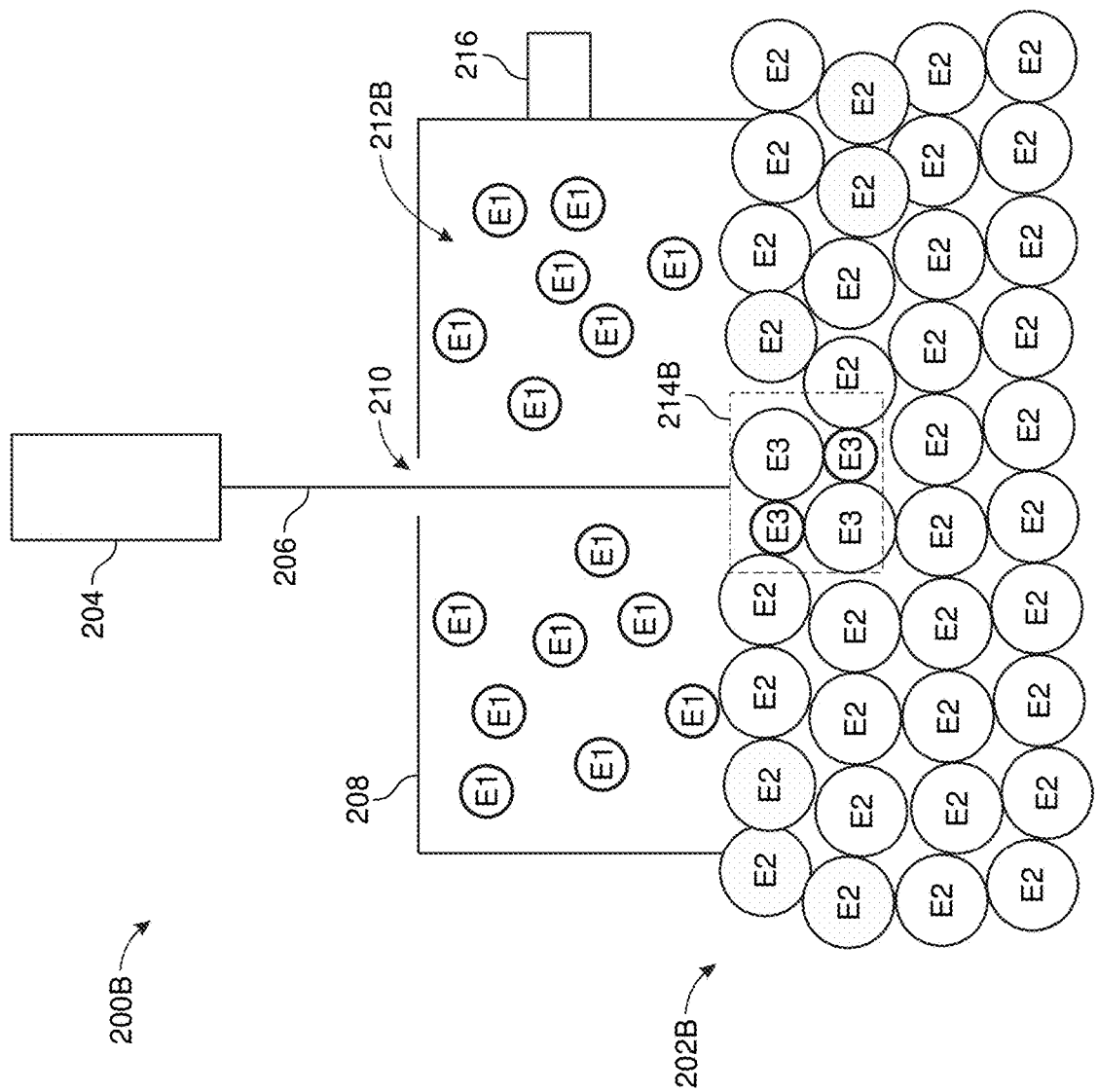

Referring to FIG. 2B, the material 202B of the system 200B having the altered surface portion 214B with the altered surface chemistry is shown. In this embodiment, the laser pulse 206 has altered the surface chemistry from the second element composition (e.g., titanium in this example) to the altered surface chemistry, for example, to a third element composition (e.g., titanium nitride in this example). As a result of the interaction, the gaseous mixture 212B after the interaction may contain less of the first element composition (e.g., nitrogen in this example) than the gaseous mixture 212A before the interaction since some of the first element composition (e.g., nitrogen in this example) binds to the second element composition (e.g., titanium), as shown in the altered surface portion 214B. Embodiments herein may alter the second element composition to a third element composition having a desired characteristic, for example, improved hardness (e.g., titanium nitride), corrosion prevention (e.g., titanium ceramide, titanium carbide), or induce photocatalysis (e.g., titanium dioxide). For example, as explained above, titanium nitride is extremely hard and, therefore, may provide advantages over titanium, especially when used as a bearing surface. In embodiments, the pulsed laser 204 used to alter the surface chemistry may be a fiber pulsed laser having the following parameters: a spot size of approximately 70 µm, a pulse duration of approximately 700 fs, a pulse energy of approximately 32 µJ, an average power of 3.2 W, a pulse frequency of approximately 100 kHz and wavelength of 1550 nm. This, however, is only an example of a pulsed laser capable of altering the surface chemistry of the surface portion 214A, 214B. Other pulsed lasers having other parameters may be used, as explained above in connection with FIGS. 1A and 1B.

Figure 3:
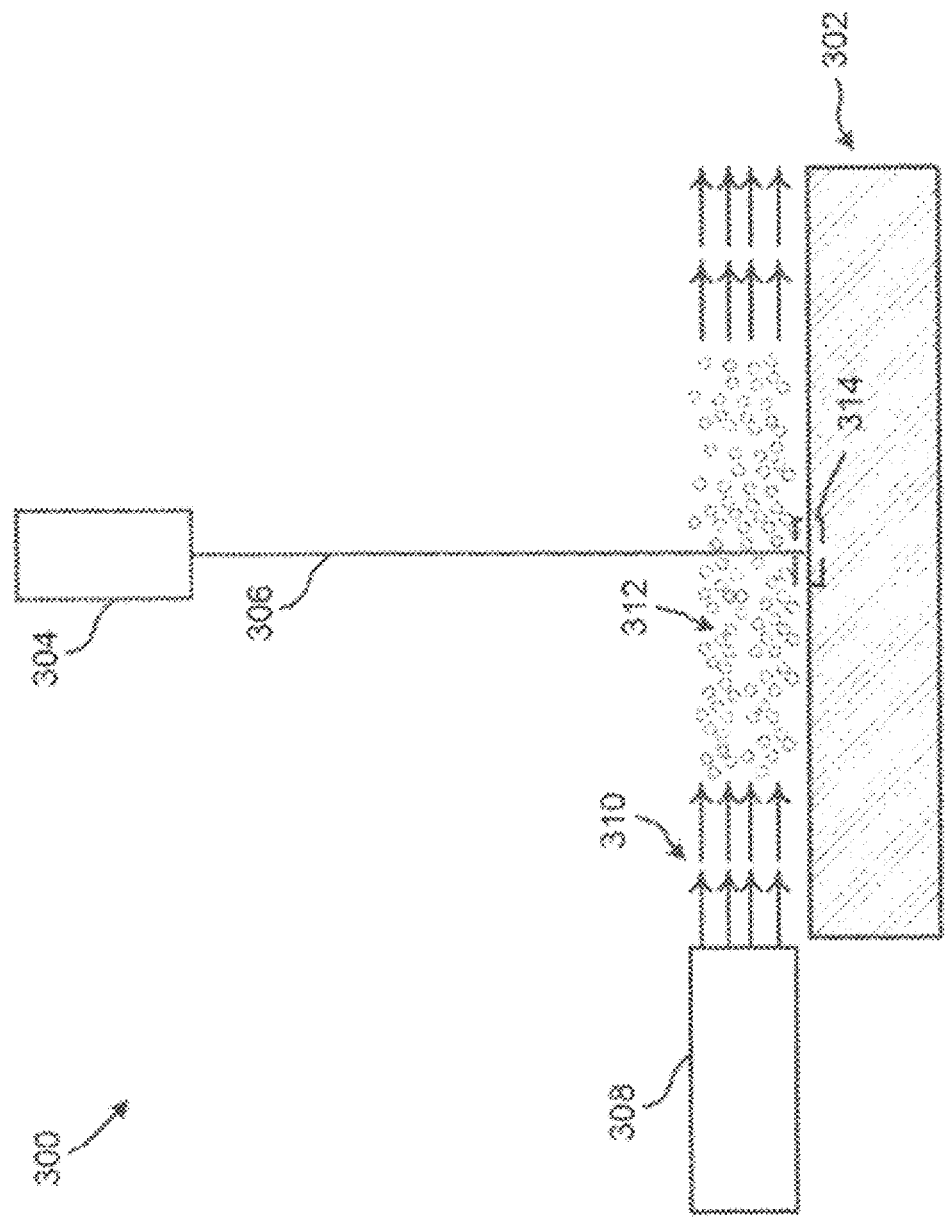
FIG. 3 is a diagram illustrating another example system for modifying the surface chemistry and surface profile of a material, in accordance with embodiments of the present disclosure.

FIG. 3 is a diagram illustrating another example system 300 for modifying the surface chemistry of a material 302, in accordance with embodiments of the present disclosure. The system 300 includes a pulsed laser 304 that emits at least one laser pulse 306, a gaseous mixture introducer 308, and a material 302. The material 302, the pulsed laser 304, and gaseous mixture 312 may have some or all same characteristics, respectively, as the material 102, the pulsed laser 104, and the gaseous mixture 112 that are described in relation to FIGS. 1A-1B above. In embodiments, the gaseous mixture introducer 308 introduces a gaseous mixture 312 (which may be substantially similar to the gaseous mixture 112 of FIG. 1A) that has a non-atmospheric composition over a surface portion 314 of the material 302. To do so, in some embodiments, the gaseous mixture introducer 308 may emit the gaseous mixture 312 (e.g., through a nozzle or opening) and include a fan or other mechanism that transports the gaseous mixture 312 from the gaseous mixture introducer 308 to the surface portion 314 using a transport system 310. As another example, the gaseous mixture introducer 308 may be a pressurized nozzle that emits the gaseous mixture 312 and transports the gaseous mixture 312 from the gaseous mixture introducer 308 to the surface portion 314. The gaseous mixture introducer 308 may induce a laminar flow of the gaseous mixture 312. In other embodiments, the gaseous mixture introducer 308 does not emit the gas, but instead includes a fan or other mechanism that transports the gaseous mixture 312 emitted from another device (not shown) to the surface portion 314 using a transport system 310. Exemplary transport systems include conduits and other devices for directing a gaseous mixture. In even other embodiments, the gaseous mixture introducer 308 emits the gaseous mixture 312 and another device (not shown) includes a fan, a conduit, or other device to direct the gaseous mixture 312 to the surface portion 314 using a transport system 310. In even other embodiments, the gaseous mixture introducer 308 emits the gaseous mixture 312 over the surface portion 314 and a fan or other device is not needed to transport the gaseous mixture 312 to the surface portion 314.

Similar to the system 100a shown in FIG. 1A, after the gaseous mixture 312 is over the surface portion 314, the laser pulse 306 from the pulsed laser 304 is directed through the gaseous mixture 312 onto the surface portion 314. The energy irradiance of the laser pulse 306 is sufficient to convert the surface portion 314 to a plasma state. While the surface portion 314 is in a plasma state, a portion of the gaseous mixture 312 located near the surface portion 314 interacts with the surface portion 314. After the laser pulse 306 no longer irradiates the surface portion 314, the interaction of the surface portion 314 and the portion of the gaseous mixture 312 results in an altered surface chemistry of the surface portion 314.

The example system 300 shown in FIG. 3 may have some advantages over the system 100a, 100b shown in FIGS. 1A-1B. In the example system 100a, 100b shown in FIGS.

1A-1B, the aperture 110 may interfere with rastering the pulsed laser 104 over a portion of the material 102 that is larger than the surface portion 114. The system 300 shown in FIG. 3, however, may avoid this problem since the system 300 does not include an aperture that the laser pulse 306 is directed through. As such, the pulsed laser 304 of system 300 may be rastered over a portion of the material 302 that is larger than the surface portion 114 in FIG. 1A or 1B.

Additionally or alternatively, a liquid, plasma, and/or solid substance 116 may be used in place of, or in addition to, the gaseous mixture 312, as described above in relation to FIG. 1B.

FIG. 4A is a diagram illustrating an example system 400A for modifying a specific surface chemistry of a material 402A, in accordance with embodiments of the present disclosure. The system 400A includes a pulsed laser 404 that emits at least one laser pulse 406, a gaseous mixture introducer 408 for introducing a gaseous mixture 412A over a surface portion 414A of a material 402A. The pulsed laser 406 may have some or all same characteristics the pulsed laser 104 described in relation to FIGS. 1A-1B above. In embodiments, the gaseous mixture introducer 408 has some or all of the same characteristics as the gaseous mixture introducer 308 shown in FIG. 3. For example, the gaseous mixture introducer 408 can emit the gaseous mixture 412A and have a transport system 410 to transport the gaseous mixture 412A over the surface portion 414A, similar to the gaseous mixture introducer 308 shown in FIG. 3. Exemplary transport systems include conduits and other devices for directing a gaseous mixture. When the gaseous mixture 412 is over the surface portion 414A, the laser pulse 406 from the pulsed laser 404 is directed through the gaseous mixture 412A onto the surface portion 414A. As shown, the surface portion 414A is the top surface of the material 402A. In this example, the pulsed laser 404 is rastered over the top surface of the material 402 to alter the surface chemistry of the entire top surface of the material 402.

Figure 4B:
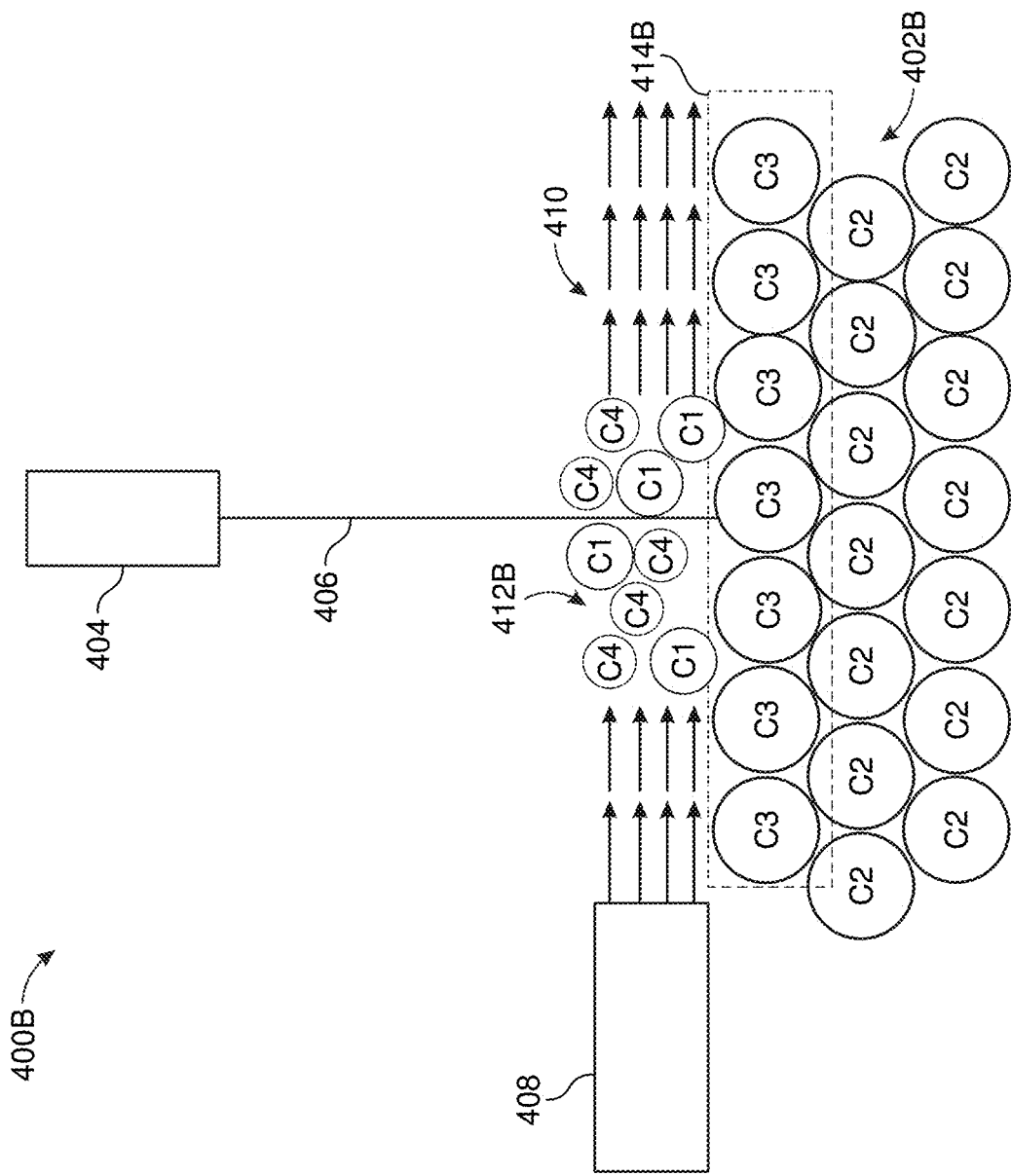

In this example, the gaseous mixture 412A includes a first chemistry (C1) selected to interact with the surface portion 414A, when the surface portion 414A is irradiated with the at least one laser pulse 406, to alter the surface chemistry of the surface portion 414A from a second chemistry (C2) to an altered surface chemistry (C3). For example, the surface chemistry of the surface portion 414A is altered from $Fe_2O_3$, (i.e., red iron oxide) as the second chemistry to $Fe_3O_4$ (i.e., Magnetite) as the altered surface chemistry. Exemplary gaseous mixtures 412A that may be used include, but are not limited to, 100% Argon (as illustrated in FIGS. 4A, 4B), 100% Nitrogen, 100% Oxygen, 100% Hydrogen, or a combination thereof. The gaseous mixture 412A may be composed of 100% of the first chemistry (e.g., argon in this example), in other embodiments, the gaseous mixture has a concentration of less than 100% of the first chemistry. Similarly, while the surface chemistry of the surface portion 414A is shown to be composed of 100% of the second chemistry (e.g., $Fe_2O_3$ in this example), in other embodiments, the surface chemistry has a concentration of less than 100% of the second chemistry.

The energy irradiance of the laser pulse 406 is sufficient to convert the second chemistry (e.g., $Fe_2O_3$ in this example) of the surface portion 414A to a plasma state. While the surface portion 414A is in a plasma state, a portion of the first chemistry (e.g., argon in this example) in the gaseous mixture 416A located near the surface portion 414A may interact with the second chemistry (e.g., $Fe_2O_3$ in this example) of the surface portion 414A. After the laser pulse 406 no longer irradiates the surface portion 414A, the interaction of the second chemistry and the first chemistry may result in an altered surface chemistry of the surface portion 414A.

Referring to FIG. 4B, the material 402B of system 400B with an altered surface portion 414B is shown. In this embodiment, the laser pulse 406 has altered the surface chemistry of the surface portion 414A from the second chemistry (e.g., $Fe_2O_3$) to the altered surface chemistry (e.g., $Fe_3O_4$ (i.e., Magnetite) in this example). As a result of an interaction of the surface chemistry with the gaseous mixture 412A, the gaseous mixture 412B after the interaction may contain ejected elements (C4) since some oxygen may be ejected from the surface chemistry of the altered surface portion 414B. For example, after interaction of argon with $Fe_2O_3$, the gaseous mixture 412B may include more oxygen than the gaseous mixture 412A prior to interaction since some oxygen may be ejected from the surface chemistry of the altered surface portion 414B. As explained above, Magnetite is environmentally resistant and, therefore, provides advantages over red iron oxide. In embodiments, the pulsed laser 404 used to alter the surface chemistry may be a fiber pulsed laser having the following parameters: a spot size of approximately 70 µm, a pulse duration of approximately 700 fs, a pulse energy of approximately 32 µJ, an average power of 3.2 W, a pulse frequency of approximately 100 kHz and wavelength of 1550 nm. This, however, is only an example of a pulsed laser capable of altering the surface chemistry of the surface portion. Other pulsed lasers having other parameters may be used, as explained above in FIGS. 1A and 1B.

FIG. 5 is a diagram illustrating another system 500 for modifying the surface chemistry of a material 502, in accordance with the embodiments of the present disclosure. The system 500 includes a pulsed laser 504 that emits at least one laser pulse 506 and an enclosure 508 that includes an aperture 510, a gaseous mixture 512 having a non-atmospheric composition and the material 502. The material 502, the pulsed laser 504, the aperture 510 and the gaseous mixture 512 may have some or all same characteristics, respectively, as the material 102, the pulsed laser 104, the aperture 110 and the gaseous mixture 112 that are described in relation to FIGS. 1A-1B above.

Alternatively and similar to above, in embodiments, the aperture 510 is replaced by a window or other material that is generally optically transparent to the wavelength of the laser pulse 506. As such, the energy irradiance of the laser pulse 506 can be project through the window or other material that is generally optically transparent at the wavelength of the laser pulse 506 and be focused on the surface portion 514.

Similar to the embodiments described above, the laser pulse 506 from the pulsed laser 504 is directed through the aperture 510 and the gaseous mixture 512 onto the surface portion 514. The energy irradiance of the laser pulse 506 is sufficient to convert the surface portion 514 to a plasma state. While the surface portion 514 is in a plasma state, a portion of the gaseous mixture 512 located adjacent the surface portion 514 interacts with the surface portion 514. After the laser pulse 506 no longer irradiates the surface portion 514, the interaction of the surface portion 514 and the portion of the gaseous mixture 512 results in an altered surface chemistry of the surface portion 514.

Additionally, the system 500 may include a filter 516 coupled to the enclosure 508. In embodiments, the filter 516 is capable of filtering an undesirable substance from the gaseous mixture 512, similar to the filters 117, 216 (FIGS.

1 and 2, respectively). Accordingly, the interaction between the gaseous mixture 512 and the surface portion 514 may be more controlled.

In contrast to the system 100a, 100b, shown in FIGS. 1A-1B, the material 502 may be inserted into the enclosure 508 to contain the liquid, gas, plasma or other material. An advantage of the embodiment shown in FIG. 5 may be that the enclosure 508 does not need to be secured to the material 502 at the edges of enclosure 508 and. Accordingly, the use of enclosure 508 may provide for an easier application and may also provide better protection against leaks of the gaseous mixture 512. However, the embodiment shown in FIGS. 1A-1B may provide an advantage over the embodiment shown in FIG. 5 in applications where it is not practical to insert the material into an enclosure such as enclosure 508. This may occur, for example, where the device being treated is too large to fit within an appropriate enclosure 508 or where it is desirable to avoid the gaseous mixture 512 (or other fluid or composition) from contacting certain other surfaces of the subject medical device.

As with the embodiments of FIGS. 1A-1B, a liquid, plasma, and/or solid substance 116 may be used in place of, or in addition to, the gaseous mixture 512, with enclosures such as enclosure 508.

FIG. 6 is a diagram illustrating another example system 600 for modifying a surface chemistry, in accordance with embodiments of the present disclosure. The system 600 includes a pulsed laser 604 that emits at least one laser pulse 606, an enclosure 608 that includes a non-atmospheric composition and a material 602. The material 602, the pulsed laser 604 and the gaseous mixture 612 may have some or all same characteristics, respectively, as the material 102, the pulsed laser 104 and the gaseous mixture 112 that are described in relation to FIGS. 1A-1B above.

Similar to the embodiments described above, the laser pulse 606 from the pulsed laser 604 is directed through the gaseous mixture 612 onto the surface portion 614. The energy irradiance of the laser pulse 606 is sufficient to convert the surface portion 614 to a plasma state. While the surface portion 614 is in a plasma state, a portion of the gaseous mixture 612 located near the surface portion 614 interacts with the surface portion 614. After the laser pulse 606 no longer irradiates the surface portion 614, the interaction of the surface portion 614 and the portion of the gaseous mixture 612 results in an altered surface chemistry of the surface portion 614.

Additionally, the system 600 may include a filter 616 coupled to the enclosure 608. In embodiments, the filter 616 is capable of filtering an undesirable substance from the gaseous mixture 612, similar to the filters 117, 216, 516 (FIGS. 1, 2 and 5, respectively). Accordingly, the interaction between the gaseous mixture 612 and the surface portion 614 may be more controlled.

As shown, in this example the pulsed laser 604 is encased in the enclosure 608. Similar to the example system 300 shown in FIG. 3, the example system 600 shown in FIG. 6 may have some advantages over the systems 100a, 100b, 500 shown in FIGS. 1A, 1B, and 5, respectively. In particular, the pulsed laser 604 of system 600 may be rastered over a large surface portion 614 of the material 602 without an aperture (e.g., the apertures 110, 510) interfering with the laser pulse 606.

Alternatively, the embodiments shown in FIGS. 1A-1B may provide an advantage over the embodiment shown in FIG. 6 if it is not practical to insert the material into an enclosure.

As with the embodiments of FIGS. 1A-1B and FIG. 5, a liquid, plasma, and/or solid substance 116 may be used in place of, or in addition to, the gaseous mixture 612, with enclosures such as enclosure 608.

FIG. 7 is a flow diagram depicting an illustrative method 700 for modifying the surface profile and chemistry of a material to selectively promote or inhibit bioactivity in accordance with the embodiments of the present disclosure. Method 700 includes providing a material (block 702), for example, such as materials 102, 202A, 302, 402A, 502, and/or 602. The material provided may be shaped (e.g., shaped as a portion of a medical device). The material provided includes a surface portion (e.g., surface portion 114, 214, 314, 414A, 514, and/or 614) having a surface chemistry. The surface chemistry can either be a metal, a metal-alloy, a non-metal or a combination thereof. A few example types of surface chemistries of the material are the following: titanium, $Fe_2O_3$, aluminum (e.g., Aluminum 2024), copper, stainless steel (e.g., 17-4 stainless steel), carbon steel (e.g., 1018 carbon steel), a ceramic coated steel, tantalum, hafnium, zirconium, silicon and/or the like.

Method 700 further includes exposing the surface portion to, for example, a gaseous mixture having non-atmospheric composition (block 704). Additionally or alternatively, a liquid, plasma, and/or solid substance 116 may be used in place of, or in addition to, the gaseous mixture, as described above in relation to FIG. 1B. In embodiments, exposing the gaseous mixture near a surface portion of the material may include enclosing the surface portion and a portion of the space adjacent to the surface portion and adding the gaseous mixture into the enclosure. In embodiments, enclosing the surface portion and a portion of the space adjacent to the surface portion, and adding the gaseous mixture into the enclosure may be done in a similar manner to the systems 100a, 100b, 500, 600 shown in FIGS. 1A, 1B, 5 and 6 above which illustrate the portion of space adjacent to the surface portion including the gaseous mixture.

In other embodiments, exposing the surface portion to the gaseous mixture may include injecting the gaseous mixture to a space adjacent to the surface portion. In embodiments, injecting the gaseous mixture to a space adjacent to the surface portion may be done in a similar manner to the system 300 shown in FIG. 3 above.

Similarly, in embodiments, the gaseous mixture can have the same composition as the gaseous mixtures 112, 212A, 212B, 312, 412A, 412B, 512, 612 described above. For example, the gaseous mixture may include a 100% concentration of nitrogen or 100% concentration of argon. Alternatively, the gaseous mixture may include a concentration of nitrogen greater than 78% or a concentration of argon greater than 50%. Gases included in the gaseous mixtures 112 may also include, but are not limited to, oxygen and/or hydrogen. However, these are only examples and not meant to be limiting. In embodiments, the gaseous mixture is chosen so that after the interaction of the gaseous mixture with the surface chemistry of the surface portion, a desired altered surface chemistry is obtained.

Method 700 also includes exposing the surface portion to at least one laser pulse while the surface portion is exposed to the gaseous mixture (block 706). The at least one laser pulse passes through the gaseous mixture onto the surface portion, thereby modifying the surface chemistry of the surface portion. As described in the FIGS. above, the energy irradiance of the laser pulse is sufficient to convert the surface portion to a plasma state. Exemplary systems using pulsed lasers to convert a surface portion to a plasma state are disclosed in U.S. application Ser. No. 14/587,455, entitled "ADHESION IMPROVEMENT VIA MATERIAL NANOSTRUCTURING OR TEXTURIZING," U.S. application Ser. No. 13/604,951, entitled "NANOSTRUCTURED MATERIALS, METHODS, AND APPLICATIONS," U.S. application Ser. No. 13/253,173, entitled "FEMTOSECOND LASER PULSE SURFACE STRUCTURING METHODS AND MATERIALS RESULTING THEREFROM," the entire disclosures of which are expressly incorporated by reference herein. While the surface portion is in a plasma state, a portion of the gaseous mixture located near the surface portion interacts with the surface portion. After the laser pulse no longer irradiates the surface portion, the interaction of the surface portion and the portion of the gaseous mixture results in an altered surface chemistry of the surface portion. Examples of specific chemistries that may be altered include, but are not limited to, changing titanium to titanium nitride and changing Fe2O3 to Fe3O4.

In embodiments, the pulsed laser used to emit the laser pulse has some or all of the same characteristics as the pulsed lasers 104, 204, 304, 404, 504, 604 described above in FIGS. 1-6. For example, the pulsed laser can be an ultrashort pulsed laser and include the following parameters: a duration less than or equal to 1,000 femtoseconds (fs), a wavelength between 100 nanometers (nm) and 3000 nm, angles of incidence greater than or equal to 0 degrees and less than 90 degrees, spot sizes between 50 microns and 100 microns and frequencies between 50 kilohertz and 200 kilohertz. As another example, the pulsed laser can be a ultrashort pulsed laser and include the following parameters: a duration between 850 fs and 550 fs, a wavelength between 1850 nm and 1240 nm, an angle of incidence between 0 and 20 degrees, a spot size between 85 microns and 55 microns, a frequency between 120 kilohertz and 80 kilohertz, a pulse energy between 40 µJ and 25 µJ, and an average power between 4 Watts and 2 Watts. As even another example, the pulsed laser can be a ultrashort pulsed laser and include the following parameters: a duration between 770 fs and 630 fs, a wavelength between 1705 nm and 1395 nm, an angle of incidence between 0 and 10 degrees, a spot size between 77 microns and 63 microns, a frequency between 110 kilohertz and 90 kilohertz, a pulse energy between 36 µJ and 28 µJ, and an average power between 3.6 Watts and 2.8 Watts. However, these are only examples and not meant to be limiting. Instead, any pulsed laser capable of turning the surface chemistry of the material into a plasma state may be used.

In embodiments, method 700 may also include rastering at least one laser pulse over a surface of the material (block 708). An advantage to rastering the at least one laser pulse over the surface of the material is so that a larger portion of the surface chemistry may be altered. The pulsed laser emitting the at least one laser pulse may be rastered over the surface of the material at different speeds and in different patterns. For example, the pulsed laser may be rastered over the surface of the material at speeds of 10 millimeters per second (mm/s), 20 mm/s, 30 mm/s and 40 mm/s, etc. and/or in square patterns, linear patterns, cross-hatch patterns, patterns that pass over a portion of the surface multiple times, etc. Again, however, these are only examples and not meant to be limiting. Instead, any speed and/or pattern may be used, as long as the at least one laser pulse is capable of turning the surface chemistry of the material into a plasma state.

Method 700 may also include shaping the material (block 710). The material may be shaped as at least a portion of a medical device (for example, by additive and/or subtractive manufacturing). It can also be understood the step for providing a material (block 702) includes providing a shaped material.

The systems and method described herein may also alter the surface profile of a material. The following examples shown in FIGS. 8A-8G and described herein are examples of surface profile alteration wherein the surface portion being altered was exposed to an atmospheric gaseous mixture. Similar surface profile structures are produced when the surface portion being altered is exposed to a non-atmospheric gaseous mixture.

Figure 8A:
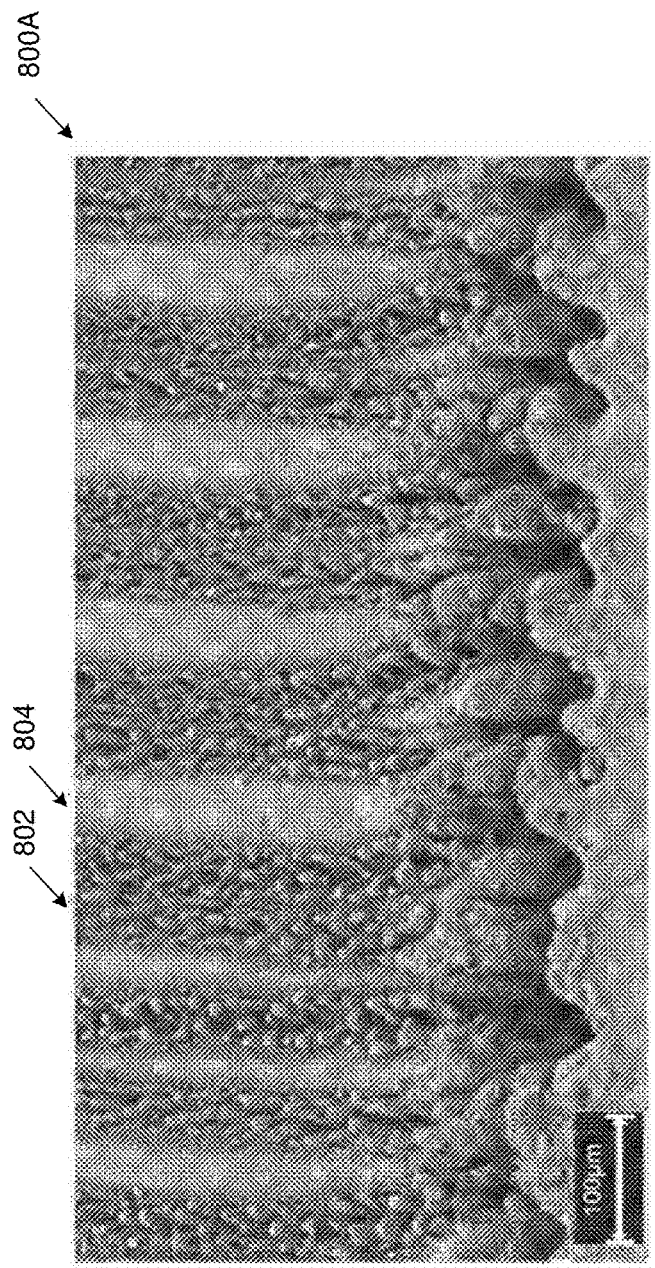
FIGS. 8A-8G are diagrams illustrating example surface profiles of a material, in accordance with embodiments of the present disclosure.
Figure 8B:
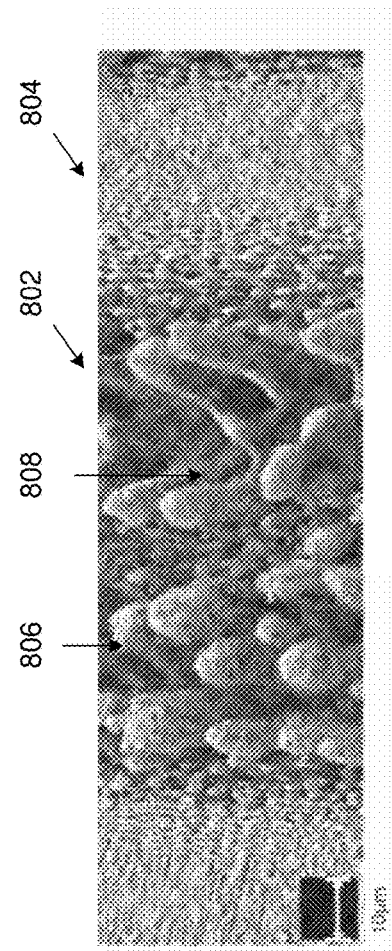
Figure 8C:
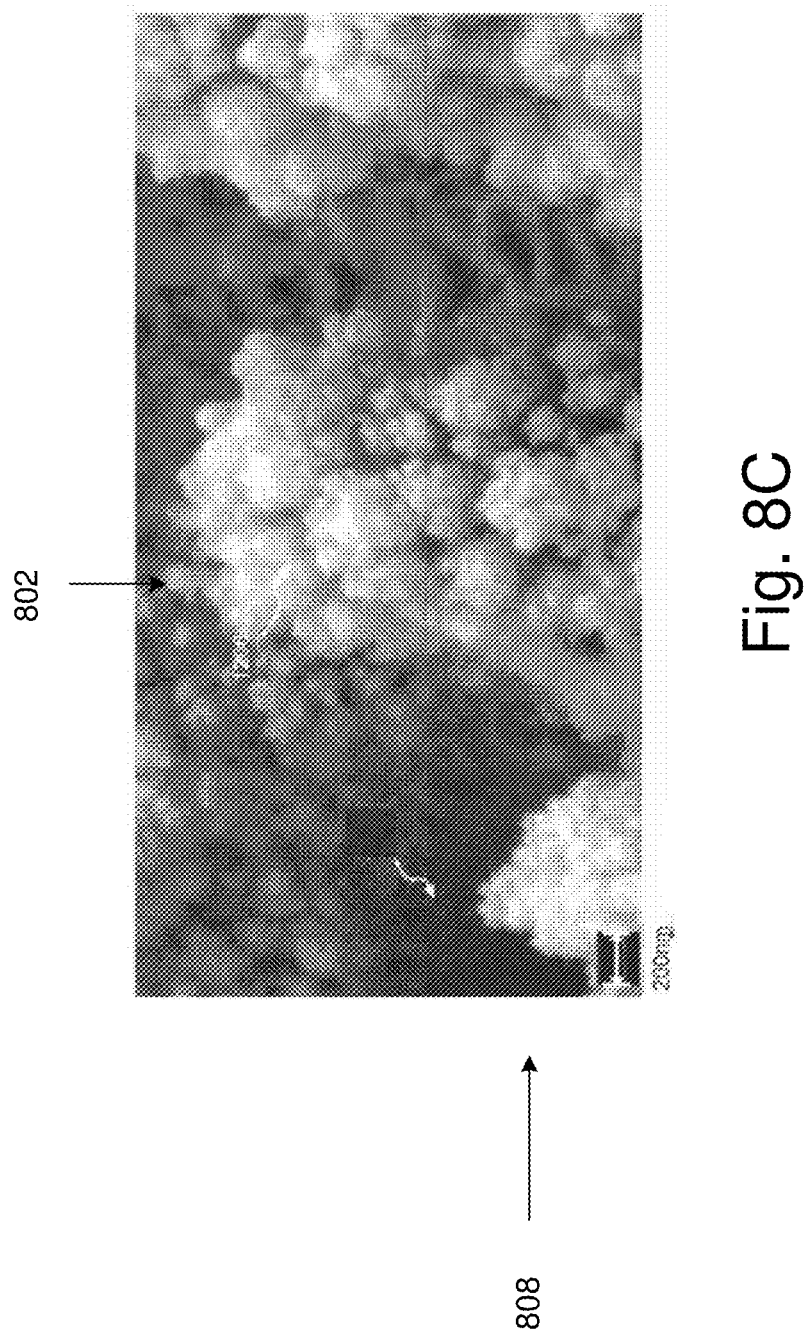

FIGS. 8A-8C are magnified images, of modified surface profiles of a nickel alloy that were produced having an atmospheric gaseous mixture adjacent to the surface portion to be altered. FIG. 8C represents an image at double magnification of FIGS. 8A-8B. As shown, the surface 800A includes two portions 802, 804 that have different surface profiles. The first portion 804 was not exposed to laser pulses and the second portion 802 was exposed to laser pulses. The first portion 804, which was not exposed to laser pulses, has a surface profile that is generally flat and does not contain protrusions that extend out from the surface 800A. In contrast, the second portion 804 includes a plurality of structures that extend out from the surface 800A.

As can be seen in FIGS. 8B-8C, the structures 806 are generally less than 10 µm in width and less than 20 µm in height. Additionally, the structures 806 may include cavities 808. The structures 806 and cavities 808 are irregularly shaped. As explained above, due to the structures 806 and cavities 808, the surface area of the surface 800A is increased and, therefore, the adhesion mechanical interlocking characteristics of the surface 800A have increased.

Figure 8D:
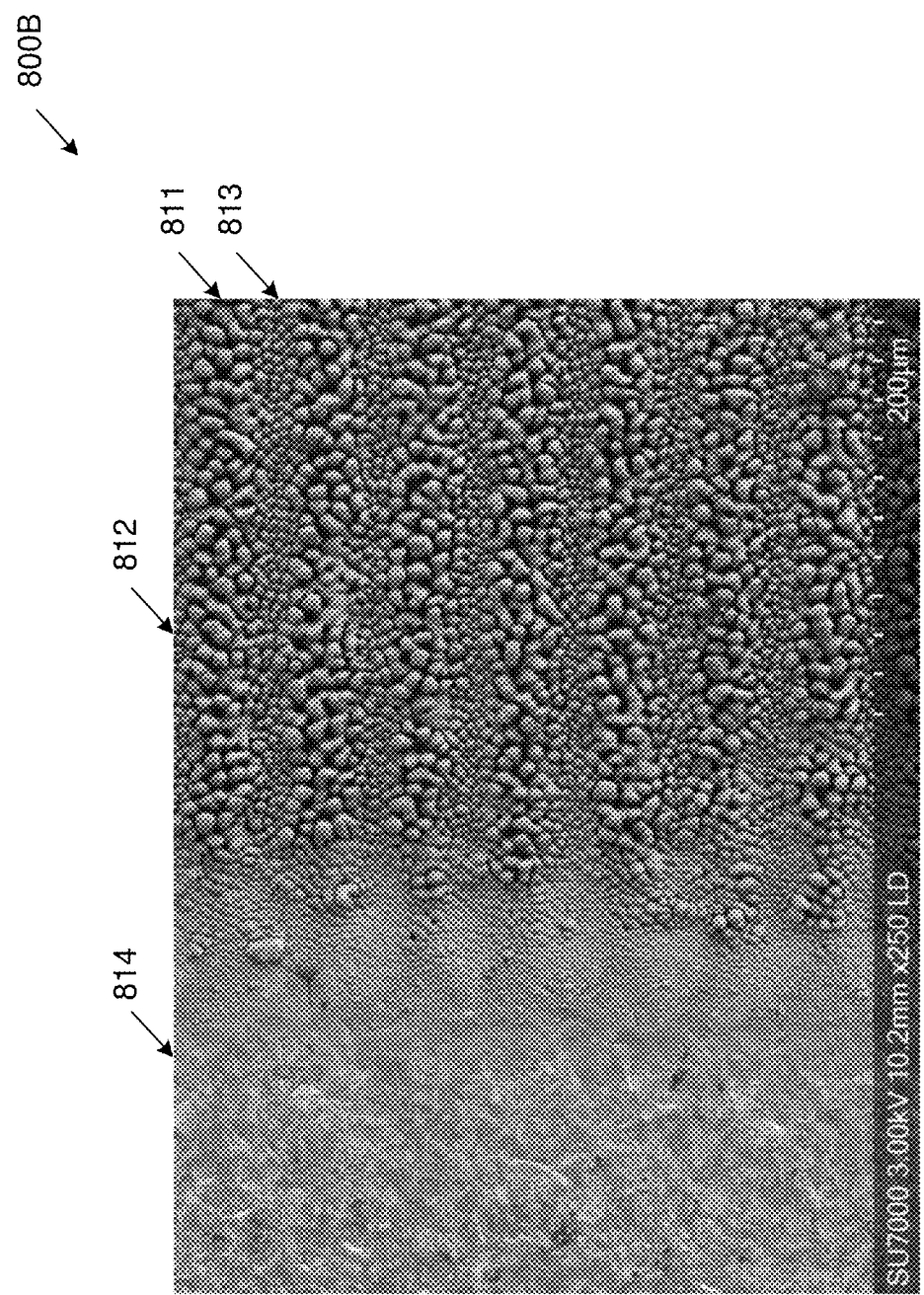
Figure 8E:
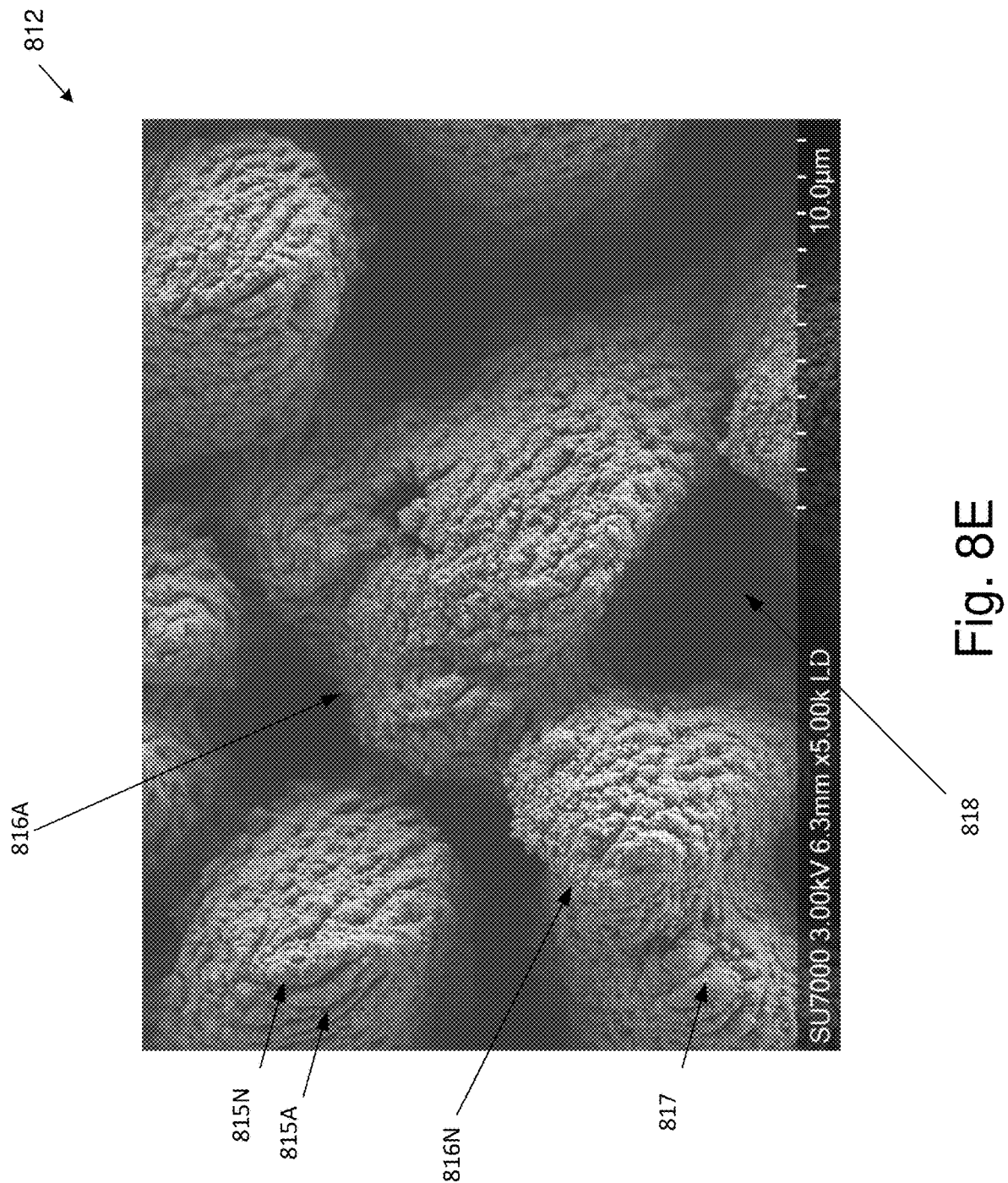

FIGS. 8D and 8E are magnified images of an example surface profile that are modified in accordance with embodiments of the disclosed technology. The modified surface profiles shown in FIGS. 8D and 8E have microstructures and nanostructures produced based on atmospheric gaseous mixture adjacent to the surface portion to be altered. As shown in FIG. 8D, the surface 800B includes two portions 812, 814 that have different surface profiles. The first portion 814 was not exposed to laser pulses and the second portion 812 was exposed to laser pulses. The first portion 814, which was not exposed to laser pulses, has a surface profile that is generally flat and does not contain protrusions or structures that extend out from the surface 800B. In contrast, the second portion 812 includes a plurality of structures that extend out from the surface 800B. The second portion 812 includes trenches 811 between peaks 813 extending along surface 800B. As can be seen in FIG. 8D, the second portion 812 includes structures on a micro-scale (e.g. microstructures), with larger structures within the trenches 811 and smaller structures 813 on peaks between the trenches. In this example, the trenches 811 are generally less than 60 µm from peak 813 to peak 813. Additionally, in the example of FIG. 8D, the trenches are generally between 40 µm and 60 am from peak 813 to peak 813.

FIG. 8E represents an image at 20 times additional magnification of a portion of a trench 811 of FIG. 8D. As can be seen in FIG. 8E, the surface 812 includes a plurality of structures 816A-N (collectively referred to as structures 816) and structures 815A-N (collectively referred to as structures 815). The structures 816 may vary, but are generally less than 10 µm in width. For example, as shown in FIG. 8D, the structures 816 are between 5 µm and 15 µm; however, larger or smaller structures are possible (e.g., 0.1 am to 999 µm as described above). Additionally, the structures 816 may include cavities 818. Furthermore, the structures 816 may include structures 815 formed on structures 816. The structures 815 may vary, but are generally less than 1 μm in width. For example, the structures 815 may be between 0.1 nm to 999 nm, as described above. The structures 815 may also include cavities and may include further even smaller structures 817 thereon. Additionally, while not shown in FIG. 8E, the peaks 813 may include structures 815-817 similar to those described above, except that the structures 815 may be smaller than those in in the trench 811 shown in FIG. 8D. The structures 815, 816, 817, and respective cavities are irregularly shaped. As explained above, due to the structures 815, 816, 817, and respective cavities, the surface area of the surface 800B is increased and, therefore, the adhesion mechanical interlocking characteristics of the surface 800B have increased.

Figure 8F:
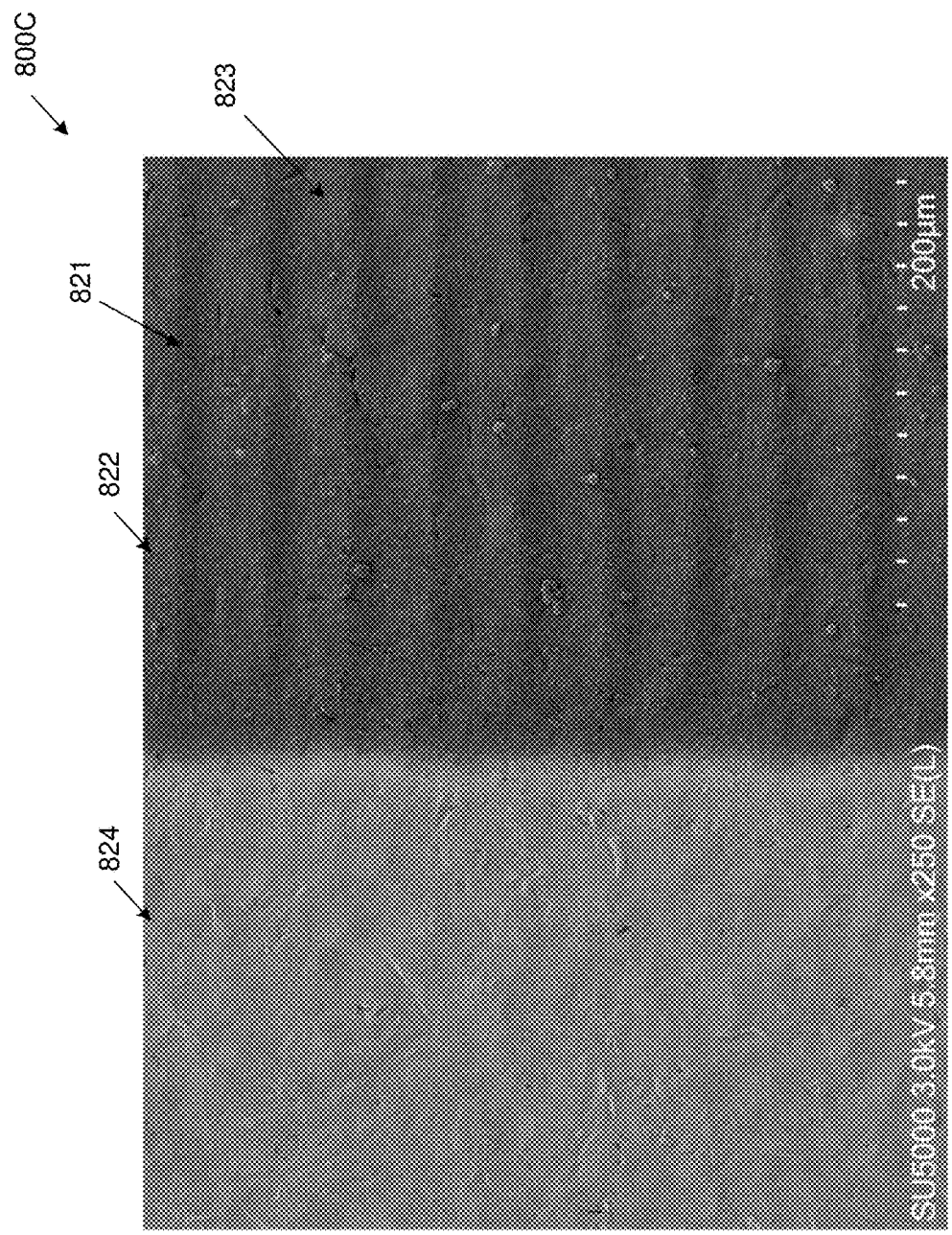
Figure 8G:
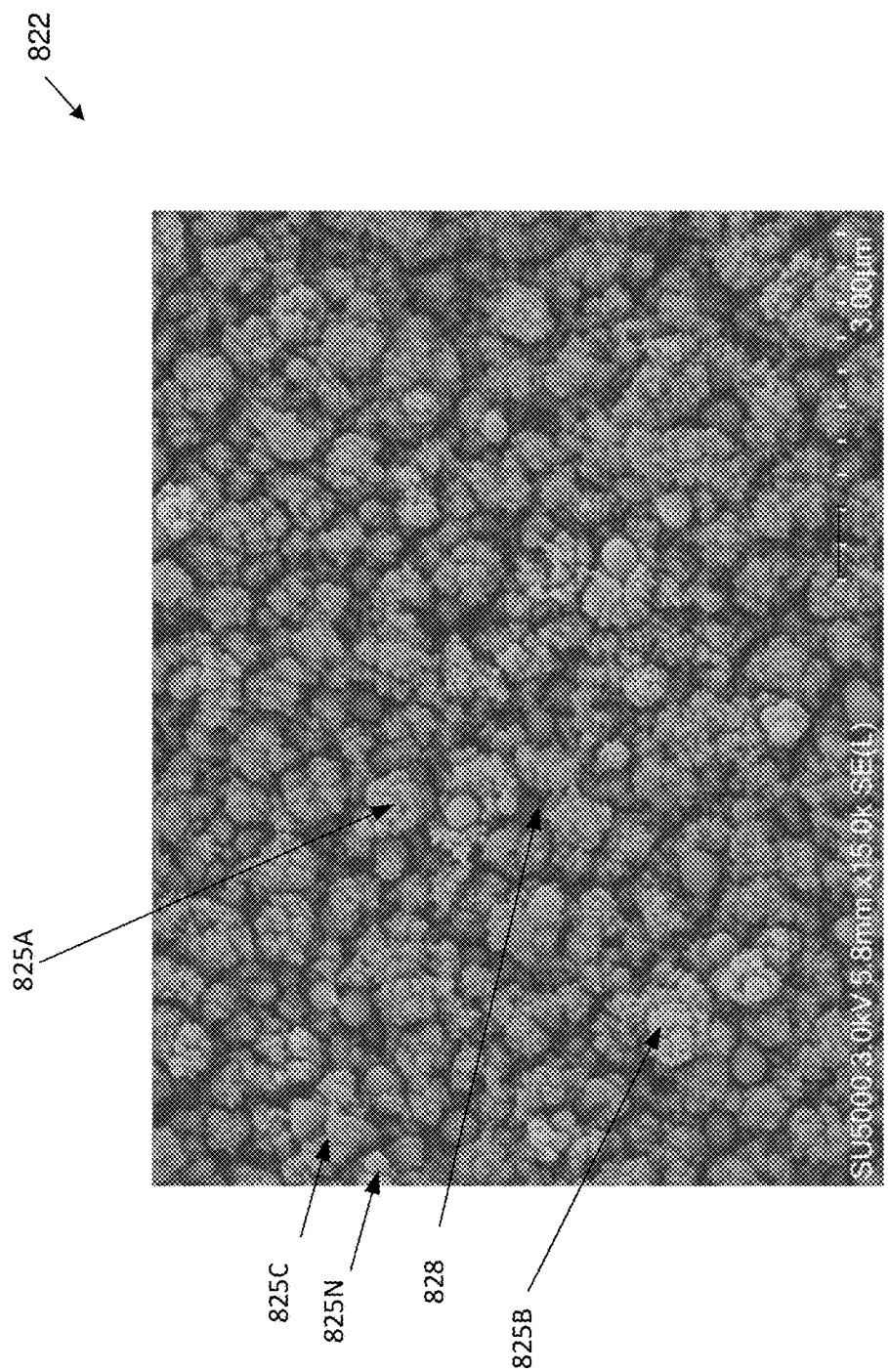

FIGS. 8F and 8G are magnified images of an example surface profile that are modified in accordance with embodiments of the disclosed technology. The modified surface profiles shown in FIGS. 8F and 8G include nanostructures produced based on atmospheric gaseous mixture adjacent to the surface portion to be altered. As shown, the surface 800C includes two portions 822, 824 that have different surface profiles. The first portion 824 was not exposed to laser pulses and the second portion 822 was exposed to laser pulses. The first portion 814, which was not exposed to laser pulses, has a surface profile that is generally flat and does not contain protrusions or structures that extend out from the surface 800C. In contrast, the second portion 822 includes a plurality of structures that extend out from the surface 800C. The second portion 822 includes trenches 823 between peaks 821 extending along surface 800C. In this example, the trenches 823 are generally less than 60 μm from peak 821 to peak 821.

FIG. 8G represents an image at approximately 60 times magnification of a portion of surface 800C of FIG. 8F. As can be seen in FIG. 8G, the surface 822 includes a plurality of structures 825A-N (collectively referred to as structures 825). The structures 825 may vary, but are generally less than 1 μm in width. For example, as shown in FIG. 8G, the structures 825 may be less than 0.3 μm in width. Additionally, the structures 825 may include cavities 828. The structures 825 and cavities 828 are irregularly shaped. Furthermore, each structure 825 may include further smaller structures and cavities given each structure 825 an irregular, non-flat surface. As explained above, due to the structures 825 and respective cavities 828, the surface area of the surface 800C is increased and, therefore, the adhesion mechanical interlocking characteristics of the surface 800C have increased.

Figure 9B:
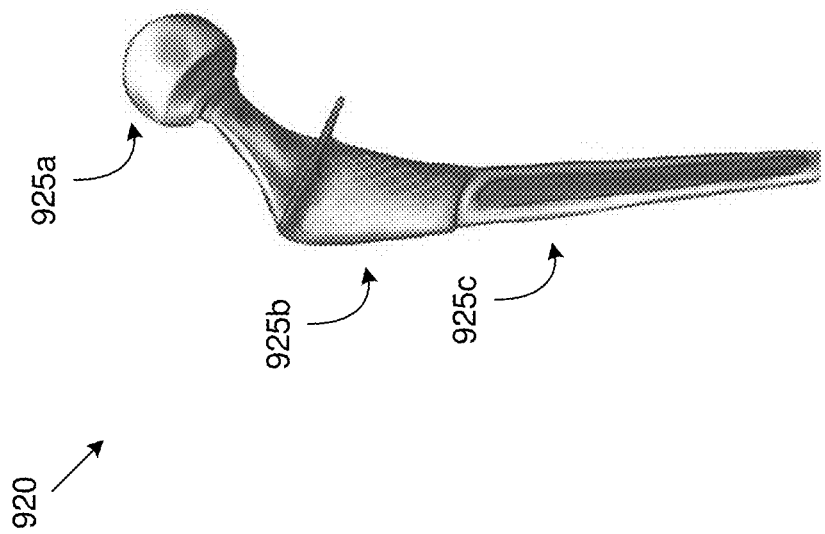
FIG. 9B depicts an illustration of an example medical device that can be processed in accordance with embodiments of the present disclosure.
Figure 9A:
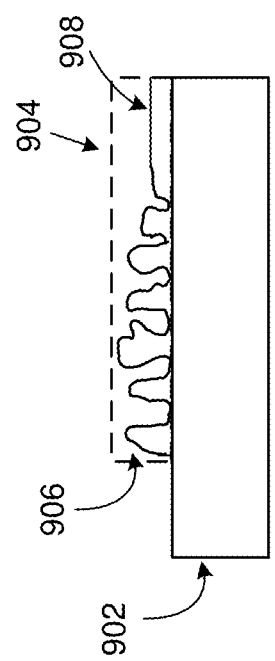
FIG. 9A is a cross-section diagram illustrating example surface profiles of material that can be included in a medical device, in accordance with embodiments of the present disclosure.

FIG. 9A is a cross-section diagram illustrating example surface profiles of material that can be included in a medical device, in accordance with embodiments of the present disclosure. Referring to FIG. 9A, a diagram illustrating an example modified surface profile 904 of a material 902 after a laser pulse (e.g., laser pulse 106, 206, 306, 406, 506, 606) of a pulsed laser (e.g., pulsed laser 104, 204, 304, 404, 504, 604) is incident on the material 902 is shown. With reference to FIGS. 1A-1B, surface profile 904 of material 902 can correspond to surface portion 114 of material 102, or other surface profiles described herein. As shown, the modified surface profile 904 includes a plurality of structures 906 extending out from the surface of the material 902. The plurality of structures 906 may have the effect of increasing the surface area of the modified surface profile 904 relative to a flat surface profile. The plurality of structures 906 may have the effect of increasing the bioactivity of the modified surface profile 904 relative to a flat surface profile. As shown in the figure, the various structures 906 can include one or more heights or depths, which may be at, above, and/or below the original surface level. In some embodiments, it may be an object of aspects of the present disclosure to reduce or minimize the structures or otherwise decrease the surface area or increase the smoothness of the of the modified surface profile. As such, relatively smooth portions 908 can be created by embodiments of the present disclosure, where the smooth portions 908 are smoother, with a smaller surface area per area footprint (e.g., the projection of the surface profile of 904 onto material 102) compared to the portions of the material 102 having structures 906. In some embodiments, a material with a rough surface profile can be shaped into a smoother surface.

In embodiments, an ultrashort pulse laser (USPL) system can be used to create the structures 906. In embodiments, the USPL has a laser pulse duration less than 1000 femtoseconds. When the laser pulse irradiates the surface of the material for a short period of time, the laser athermally converts the surface material to a plasma state. Then, the material in the plasma state loses energy and produces the structures 906. During this process, the thermal effects on the surface of the material 802 are likely less than the thermal effects produced using a non-ultrashort pulse laser that has similar other non-pulse duration parameters to the USPL, so that areas surrounding the surface portion 904 that is irradiated experience less heat transfer. On the contrary, areas surrounding the surface of the material would experience thermal effects if the laser pulse had a longer duration.

FIG. 9B depicts an illustration of an example medical device that can be processed according to aspects of the present disclosure. A medical device 920 can include one or more surface areas (925a, 925b, 925c shown) of the medical device. Various areas of the medical device can be processed with different laser parameters.

Figure 10:
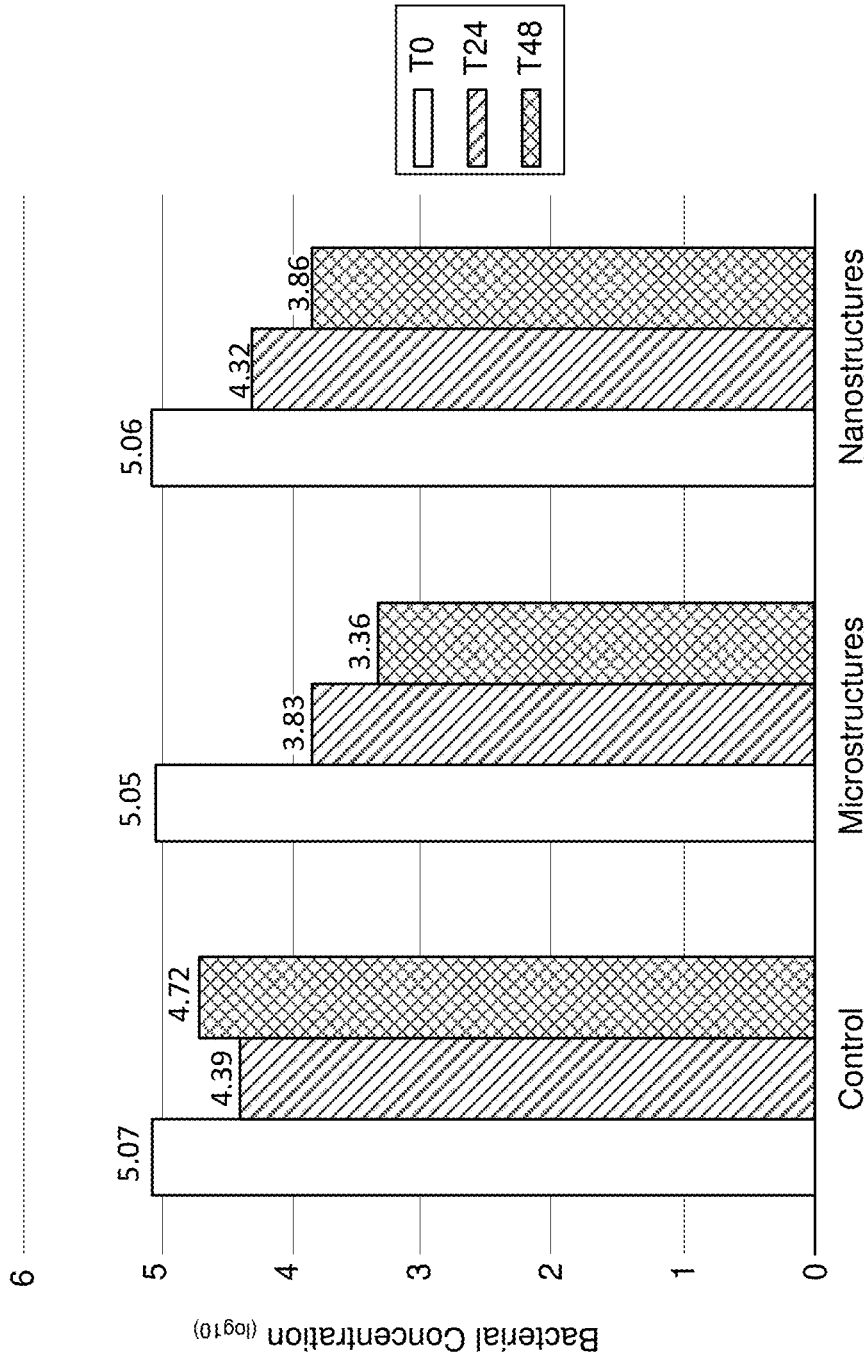
FIG. 10 is bar graph of experimental results of bacterial viability on example material surfaces modified according to embodiments of the present disclosure compared to a material surface modified according to conventional techniques.

As alluded to above, the systems and method described herein may be utilized to alter a surface profile of a material so to inhibit bioactivity on the surface. For example, FIG. 10A provides an example bar graph of experimental results of surface profile alteration that inhibits bacterial viability on a surface of a material. The bar graph of FIG. 10 shows quantitative results of bacterial viability on surface profiles that have been modified, in accordance with embodiments disclosed herein, compared to a control surface at three times following alteration: zero hours (T0) after alteration, 24 hours (T24) after alteration, and 48 hours (T48) after alteration. Particularly, FIG. 10 illustrates bacterial viability on a material surface modified to include microstructures and a material surface modified nanostructures, according to embodiments disclosed herein, while the control surface was modified using a conventional glass bead-blasting technique. The material for each experimental setup was titanium 6-4 (referred to as Ti 6-4 or Ti-6Al-4V) and measured bacteria concentration of *Staphylococcus aureus* on the modified surface, However, similar results would occur for other materials (e.g., aluminum 2024, aluminum 5083, nickel, tungsten, cobalt-chromium, stainless steel, steel HY80, steel HY100, 1018 carbon steel, titanium, titanium 6-4, superalloys such as Monel and Inconel, alloys of these metals, etc.) and for other types of bacteria. Further, the experimental results would be similar for surface profile structures provided by any of the systems disclosed here, for example, systems 100a, 100b, 200A, 200B, 300, 400A, 400B, 500, and/or 600, or from method 700.

The experimental results shown in FIG. 10 illustrates that the embodiments disclosed herein can be utilized to advantageously inhibit bioactivity on a surface. As shown in FIG.

10, the concentration of *Staphylococcus aureus* diminishes on a logarithmic scale over a 48 hour period to a greater degree than provided by the control surface. For example, material surfaces modified according to the embodiments disclosed herein provided a passive 1.5 to 2 logarithmic reduction in bacterial concentration, compared to that achieved by the control surface. While autoclaving techniques (e.g., sterilization methods) may yield up to 6 logarithmic reduction, these techniques are active or nonpassive and require action on the part of a medical professional. Thus, the passive approach of surface alteration, according to embodiments disclosed herein, is appealing to medical professionals by providing a passive method for inhibiting bacterial growth that improves the reduction in bacterial viability (e.g., reduces the bacterial concentration over time) on the surface. While multiple embodiments are disclosed, still other embodiments of the disclosed subject matter will become apparent to those skilled in the art from the following detailed description, which shows and describes illustrative embodiments of the disclosure. Accordingly, the drawings and detailed description are to be regarded as illustrative in nature and not restrictive.

The terms "substantially" and "about" used throughout this disclosure, including the claims, are used to describe and account for small fluctuations, such as due to variations in processing. For example, they can refer to less than or equal to +5%, such as less than or equal to ±2%, such as less than or equal to +1%, such as less than or equal to ±0.5%, such as less than or equal to +0.2%, such as less than or equal to +0.1%, such as less than or equal to ±0.05%.

The term "coupled" refers to direct or indirect joining, connecting, fastening, contacting or linking, and may refer to various forms of coupling such as physical, optical, electrical, fluidic, mechanical, chemical, magnetic, electromagnetic, optical, communicative or other coupling, or a combination of the foregoing. Where one form of coupling is specified, this does not imply that other forms of coupling are excluded. For example, one component physically coupled to another component may reference physical attachment of or contact between the two components (directly or indirectly), but does not exclude other forms of coupling between the components such as, for example, a communications link (e.g., an RF or optical link) also communicatively coupling the two components. Likewise, the various terms themselves are not intended to be mutually exclusive. For example, a fluidic coupling, magnetic coupling or a mechanical coupling, among others, may be a form of physical coupling.

The term tool can be used to refer to any apparatus configured to perform a recited function. For example, tools can include a collection of one or more modules and can also be comprised of hardware, software or a combination thereof. Thus, for example, a tool can be a collection of one or more software modules, hardware modules, software/hardware modules or any combination or permutation thereof. As another example, a tool can be a computing device or other appliance on which software runs or in which hardware is implemented.

Figure 11:
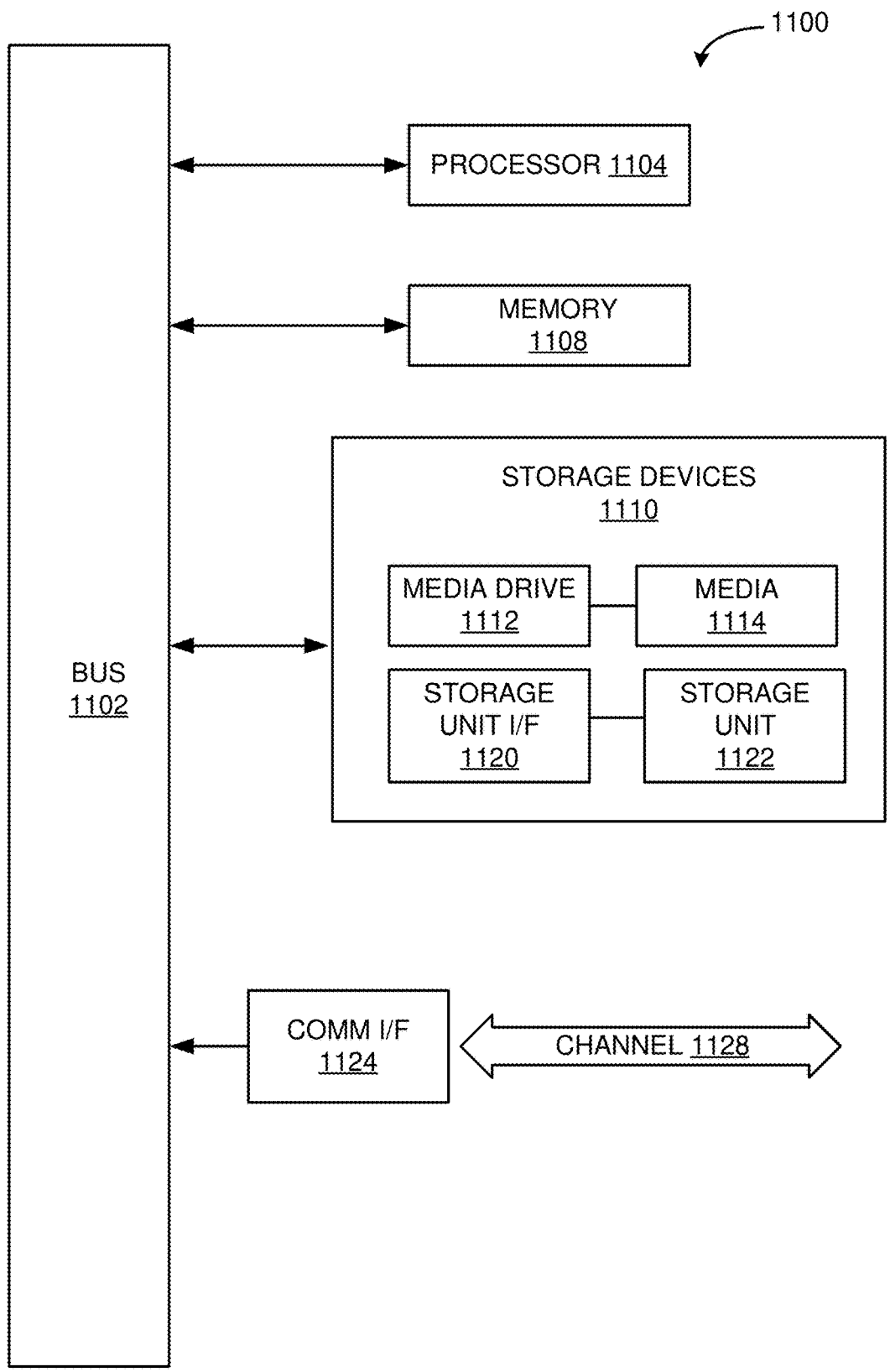
FIG. 11 is an example computing component that may be used to implement various features of embodiments described in the present disclosure.

In other words, as would be apparent to one of ordinary skill in the art after reading this description, the various features and functionality described herein may be implemented in any given application and can be implemented in one or more separate or shared elements in various combinations and permutations. Even though various features or elements of functionality may be individually described or claimed as separate elements, one of ordinary skill in the art will understand that these features and functionality can be shared among one or more common elements, and such description shall not require or imply that separate elements are required to implement such features or functionality.

Where modules or other system components (e.g., the environmental module described herein) are implemented in whole or in part using software, such software can be implemented to operate with a computing or processing system capable of carrying out the functionality described with respect to such modules or components. One such example computing system is shown in FIG. 11. Various embodiments are described in terms of this example-computing system 1100. After reading this description, it will become apparent to a person skilled in the relevant art how to implement the technology using other computing systems or architectures.

Referring now to FIG. 11, computing system 1100 may represent, for example, computing or processing capabilities found within desktop, laptop and notebook computers; hand-held computing devices (smart phones, cell phones, palmtops, tablets, etc.); mainframes, supercomputers, workstations or servers; or any other type of special-purpose or general-purpose computing devices as may be desirable or appropriate for a given application or environment. Computing system 1100 might also represent computing capabilities embedded within or otherwise available to a given device. For example, a computing system might be found in other electronic devices such as, for example, digital cameras, navigation systems, cellular telephones, portable computing devices, modems, routers, WAPs, terminals and other electronic devices that might include some form of processing capability.

Computing system 1100 might include, for example, one or more processors, controllers, control modules, or other processing devices, such as a processor 1104. Processor 1104 might be implemented using a general-purpose or special-purpose processing engine such as, for example, a microprocessor (whether single-, dual- or multi-core processor), signal processor, graphics processor (e.g., GPU) controller, or other control logic. In the illustrated example, processor 1104 is connected to a bus 1102, although any communication medium can be used to facilitate interaction with other components of computing system 1100 or to communicate externally. With reference to FIGS. 1A-1B, for example, processor 1104 can be connected to laser 104 shown in FIG. 1A-1B, environmental module, profilometer, translation and/or rotation module, and other components of system 100a, 100b by way of bus 1102 or another communication medium.

Computing system 1100 might also include one or more memory modules, simply referred to herein as main memory 1108. For example, in some embodiments random access memory (RAM) or other dynamic memory, might be used for storing information and instructions to be executed by processor 1104. Main memory 1108 might also be used for storing temporary variables or other intermediate information during execution of instructions to be executed by processor 1104. Computing system 1100 might likewise include a read only memory ("ROM") or other static storage device coupled to bus 1102 for storing static information and instructions for processor 1104.

The computing system 1100 might also include one or more various forms of information storage mechanism 1110, which might include, for example, a media drive 1112 and a storage unit interface 1120. The media drive 1112 might include a drive or other mechanism to support fixed or removable storage media 1114. For example, a hard disk drive, a floppy disk drive, a magnetic tape drive, an optical disk drive, a CD or DVD drive (R or RW), a flash drive, or other removable or fixed media drive might be provided. Accordingly, storage media 1114 might include, for example, a hard disk, a floppy disk, magnetic tape, cartridge, optical disk, a CD or DVD, or other fixed or removable medium that is read by, written to or accessed by media drive 1112. As these examples illustrate, the storage media 1114 can include a computer usable storage medium having stored therein computer software or data.

In alternative embodiments, information storage mechanism 1110 might include other similar instrumentalities for allowing computer programs or other instructions or data to be loaded into computing system 1100. Such instrumentalities might include, for example, a fixed or removable storage unit 1122 and an interface 1120. Examples of such storage units 1122 and interfaces 1120 can include a program cartridge and cartridge interface, a removable memory (for example, a flash memory or other removable memory module) and memory slot, a flash drive and associated slot (for example, a USB drive), a PCMCIA slot and card, and other fixed or removable storage units 1122 and interfaces 1120 that allow software and data to be transferred from the storage unit 1122 to computing system 1100.

Computing system 1100 might also include a communications interface 1124. Communications interface 1124 might be used to allow software and data to be transferred between computing system 1100 and external devices. Examples of communications interface 1124 might include a modem or softmodem, a network interface (such as an Ethernet, network interface card, WiMedia, IEEE 802.XX, Bluetooth® or other interface), a communications port (such as for example, a USB port, IR port, RS232 port, or other port), or other communications interface. Software and data transferred via communications interface 1124 might typically be carried on signals, which can be electronic, electromagnetic (which includes optical) or other signals capable of being exchanged by a given communications interface 1124. These signals might be provided to communications interface 1124 via a channel 1128. This channel 1128 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 1108, storage unit 1120, media 1114, and channel 1128. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing system 1100 to perform features or functions of the disclosed technology as discussed herein.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at anytime in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method for generating micro/nanoscale structures and profiles on medical devices utilizing exposure to pulsed laser radiation, comprising:
    providing a first material;
    exposing a surface portion of the first material to a plurality of laser pulses;
    tuning application of the plurality of laser pulses to form structures at the surface portion, the structures comprising:
        at least one of microscale protrusions and microscale cavities; and
        at least one of nanoscale protrusions and nanoscale cavities; and
    measuring at least one of a depth and smoothness of the surface portion,
    wherein the exposing a surface portion of the first material to the plurality of laser pulses is based on the measurement.

2. The method of claim 1, further comprising exposing the surface portion of the first material to a second material having a non-atmospheric composition, such that the plurality of laser pulses is exposed at a boundary of the surface portion of the first material and the second material.

3. The method of claim 2, wherein the second material comprises a non-atmospheric gas.

4. The method of claim 2, wherein the second material comprises at least one of a liquid, plasma, gas, and solid.

5. The method of claim 2, wherein the second material is selected to modify one or more properties of the first material, the one or more properties comprising at least one of hardness, environmental resistivity, chemical reactivity, and photocatalysis.

6. The method of claim 1, further comprising application of the plurality of laser pulses so that at least one of a first and second pattern of the structures are produced.

7. The method of claim 1, further tuning an application of the plurality of laser pulses so that at least one of desired in-vivo, ex-vivo, and in vitro behaviors of the first material are achieved.

8. The method of claim 1, wherein the at least one of microscale protrusions and microscale cavities and the at least one of nanoscale protrusions and nanoscale cavities at the surface portion inhibit at least one of organism attachment and biofilm formation.

9. The method of claim 1, wherein exposing the surface portion of the first material to plurality of laser pulses creates one or more superhydrophic structures.

10. The method of claim 1, wherein exposing the surface portion of the first material to plurality of laser pulses creates one or more superhydrophilic structures.

11. The method of claim 1, wherein the first material is one of an implant and tissue culture scaffold.

12. The method of claim 1, wherein exposing the surface portion of the first material to plurality of laser pulses promotes interfacial properties of the first material by modifying at least one of a surface profile of the surface portion and a surface chemistry of the surface portion, the method further comprising:
    applying at least one second material to at least the modified surface portion of first material to form a resultant surface composite,
    wherein the resultant surface composite comprises the at least one second material applied to the modified surface portion.

13. A method of claim 1 for generating micro/nanoscale structures and profiles on medical devices utilizing exposure to pulsed laser radiation, comprising:
    providing a first material;
    exposing a surface portion of the first material to a plurality of laser pulses; and
    tuning application of the plurality of laser pulses to form structures at the surface portion, the structures comprising:
        at least one of microscale protrusions and microscale cavities; and
        at least one of nanoscale protrusions and nanoscale cavities,
        wherein one or more of the at least one of nanoscale protrusions and nanoscale cavities are formed on one or more of the at least one of microscale protrusions and microscale cavities.

14. The method of claim 13, further comprising exposing the surface portion of the first material to a second material having a non-atmospheric composition, such that the plurality of laser pulses is exposed at a boundary of the surface portion of the first material and the second material.

15. The method of claim 13, further comprising application of the plurality of laser pulses so that at least one of a first and second pattern of the structures are produced.

* * * * *